US011484497B2

(12) United States Patent
Ragot et al.

(10) Patent No.: US 11,484,497 B2
(45) Date of Patent: Nov. 1, 2022

(54) COMPOSITION FOR MAKING A TEA BEVERAGE OR HERBAL AND VEGETABLE BROTHS

(71) Applicant: Schweitzer-Mauduit International, Inc., Alpharetta, GA (US)

(72) Inventors: Philippe Ragot, Le Mans (FR); Bernard Mompon, Vannes (FR); Cedric Rousseau, Le Mans (FR); Esther Pons, Pessac (FR); Christian Pineau, Saint Germain en Laye (FR)

(73) Assignee: Schweitzer-Mauduit International, Inc., Alpharetta, GA (US)

( * ) Notice: Subject to any disclaimer, the term of this patent is extended or adjusted under 35 U.S.C. 154(b) by 483 days.

(21) Appl. No.: 14/846,361

(22) Filed: Sep. 4, 2015

(65) Prior Publication Data

US 2015/0374624 A1 Dec. 31, 2015

Related U.S. Application Data

(63) Continuation-in-part of application No. 14/193,910, filed on Feb. 28, 2014.

(Continued)

(51) Int. Cl.
*A23F 3/18* (2006.01)
*A23L 2/08* (2006.01)
(Continued)

(52) U.S. Cl.
CPC ............. *A61K 9/0095* (2013.01); *A23F 3/30* (2013.01); *A23F 3/34* (2013.01); *A23F 3/385* (2013.01);
(Continued)

(58) Field of Classification Search
CPC ......... A61K 9/0095; A61K 36/53; A23F 3/30; A23F 3/34; A23F 3/385; A23F 5/36;
(Continued)

(56) References Cited

U.S. PATENT DOCUMENTS 3,239,117 A * 3/1966 Letchworth ........ B65D 85/8085
225/32
3,353,541 A 11/1967 Hind et al.
(Continued)

FOREIGN PATENT DOCUMENTS

CA 2814816 * 5/2012
CN 1329855 A 1/2002
(Continued)

OTHER PUBLICATIONS

Co-pending U.S. Appl. No. 15/506,620, filed Feb. 24, 2017.
(Continued)

*Primary Examiner* — Tamra L. Dicus
(74) *Attorney, Agent, or Firm* — Dority & Manning, P.A.

(57) ABSTRACT

The present invention relates to an infusion product for making a beverage, more specifically to a plant-based composition for making a beverage, and to a herbal and/or vegetable composition or bouquet garni. The plants are fruits, herbs, medicinal plants, tea, vegetables and/or spices. The invention further relates to a method for producing said compositions or infusion product, its use for making a (tea) beverage, and a (tea) beverage so obtained. Further, the present invention relates to a fiber-web, preferably a tea bag, made from said fruits, herbs, medicinal plants, tea, vegetable and/or spices.

14 Claims, 18 Drawing Sheets

Related U.S. Application Data

(60) Provisional application No. 61/770,564, filed on Feb. 28, 2013.

(51) Int. Cl.
| | | |
|---|---|---|
| *A23F 3/34* | (2006.01) | |
| *A23F 3/30* | (2006.01) | |
| *B65D 85/812* | (2006.01) | |
| *B65D 85/816* | (2006.01) | |
| *B65D 85/808* | (2006.01) | |
| *A23F 3/36* | (2006.01) | |
| *A23F 3/22* | (2006.01) | |
| *A23L 27/10* | (2016.01) | |
| *A23L 23/10* | (2016.01) | |
| *A61K 9/00* | (2006.01) | |
| *A61K 36/53* | (2006.01) | |
| *B65D 85/804* | (2006.01) | |
| *A23F 3/38* | (2006.01) | |
| *A23F 5/36* | (2006.01) | |
| *A23L 27/14* | (2016.01) | |
| *A23L 27/00* | (2016.01) | |

(52) U.S. Cl.
CPC .............. *A23F 5/36* (2013.01); *A23L 23/10* (2016.08); *A23L 27/14* (2016.08); *A23L 27/70* (2016.08); *A61K 36/53* (2013.01); *B65D 85/808* (2013.01); *B65D 85/8043* (2013.01); *B65D 85/812* (2013.01); *B65D 85/816* (2013.01)

(58) Field of Classification Search
CPC .......... A23L 23/10; A23L 27/14; A23L 27/70; B65D 85/8043; B65D 85/808; B65D 85/812; B65D 85/816
See application file for complete search history.

(56) References Cited

U.S. PATENT DOCUMENTS

| | | | |
|---|---|---|---|
| 3,386,449 A | 6/1968 | Hind | |
| 3,415,253 A | 12/1968 | Michels et al. | |
| 3,420,241 A | 1/1969 | Hind et al. | |
| 3,428,053 A | 2/1969 | Schoenbaum et al. | |
| 3,467,109 A | 9/1969 | Block et al. | |
| 3,483,874 A | 12/1969 | Hind | |
| 3,561,451 A | 2/1971 | Jacin et al. | |
| 3,760,815 A | 9/1973 | Deszyck | |
| 3,847,164 A | 11/1974 | Mattina et al. | |
| 3,860,012 A | 1/1975 | Selke | |
| 4,182,349 A | 1/1980 | Selke | |
| 4,674,519 A | 6/1987 | Keritsis et al. | |
| 4,801,464 A * | 1/1989 | Hubbard, Jr. ......... B65B 29/028 426/79 |
| 4,891,232 A | 1/1990 | Dahl | |
| 5,099,862 A | 3/1992 | White et al. | |
| 5,529,796 A * | 6/1996 | Gobbo ...................... A23F 3/18 426/330.3 |
| 5,620,724 A * | 4/1997 | Adler ...................... A47G 19/22 426/435 |
| 5,715,844 A | 2/1998 | Young et al. | |
| 5,724,998 A | 3/1998 | Gellatly et al. | |
| 5,765,570 A | 6/1998 | Litzinger et al. | |
| 6,761,918 B2 | 7/2004 | Pulikkottil et al. | |
| 6,818,234 B1 | 11/2004 | Nair et al. | |
| 7,001,629 B1 | 2/2006 | Mengal et al. | |
| 7,793,585 B2 | 9/2010 | Rasmussen | |
| 8,499,965 B2 | 8/2013 | Sheffield | |
| 8,597,667 B2 | 12/2013 | Mou et al. | |
| 8,734,881 B2 | 5/2014 | Yoakim et al. | |
| 9,220,296 B2 | 12/2015 | Fall et al. | |
| 9,266,663 B1 * | 2/2016 | Lee ......................... A47J 31/08 |
| 2002/0132098 A1 | 9/2002 | Miyazawa et al. | |
| 2003/0004479 A1 | 1/2003 | Ueda et al. | |
| 2003/0113411 A1 * | 6/2003 | Rose ................... B65D 85/808 426/77 |
| 2003/0187055 A1 | 10/2003 | Riker | |
| 2004/0156920 A1 * | 8/2004 | Kane ...................... A01N 65/00 424/725 |
| 2004/0180077 A1 | 9/2004 | Riker | |
| 2005/0064049 A1 | 3/2005 | Mori et al. | |
| 2005/0088632 A1 | 4/2005 | Sadi | |
| 2005/0158252 A1 | 7/2005 | Romanowski | |
| 2006/0165756 A1 | 7/2006 | Catani | |
| 2007/0199453 A1 | 8/2007 | Rasmussen | |
| 2007/0243273 A1 | 10/2007 | Dev et al. | |
| 2009/0047328 A1 | 2/2009 | Cunningham | |
| 2009/0169654 A1 * | 7/2009 | Banerjee .................. A23F 3/405 424/729 |
| 2010/0032444 A1 | 2/2010 | Sheffield | |
| 2010/0196545 A1 * | 8/2010 | Buffet ................ B65D 85/8043 426/79 |
| 2010/0210866 A1 | 8/2010 | Toyohara et al. | |
| 2010/0233322 A1 * | 9/2010 | Fukuda ..................... A23F 3/14 426/77 |
| 2011/0020512 A1 * | 1/2011 | Masutake ............. A23C 9/1524 426/329 |
| 2011/0072979 A1 * | 3/2011 | Fogg, IV ............ A47J 36/2466 99/288 |
| 2011/0236502 A1 | 9/2011 | Guillory | |
| 2012/0024161 A1 * | 2/2012 | Chen ...................... A47J 31/10 99/299 |
| 2013/0280320 A1 * | 10/2013 | Mompon ................. A23F 3/14 424/443 |
| 2014/0224265 A1 | 8/2014 | Rouillard et al. | |
| 2014/0295049 A1 | 10/2014 | Ragot et al. | |
| 2015/0037389 A1 | 2/2015 | Ragot et al. | |
| 2015/0050371 A1 | 2/2015 | Gehling et al. | |
| 2015/0056255 A1 | 2/2015 | Ragot et al. | |
| 2015/0175810 A1 | 6/2015 | Rieland | |
| 2015/0374624 A1 * | 12/2015 | Ragot ..................... A23L 23/10 426/77 |
| 2016/0255854 A1 | 9/2016 | Rousseau | |

FOREIGN PATENT DOCUMENTS

| | | | | |
|---|---|---|---|---|
| CN | 1565286 A | | 1/2005 | |
| CN | 1957777 A | | 5/2007 | |
| CN | 102919430 | | 2/2012 | |
| CN | 102422941 B | * | 12/2012 | |
| CN | 103054156 | | 4/2013 | |
| DE | 202010001912 U1 | | 3/2011 | |
| EP | 0679354 A1 | * | 11/1995 | ........... B65D 85/812 |
| GB | 1341069 | | 12/1973 | |
| JP | 09163930 A | * | 6/1997 | |
| JP | H10304822 | | 11/1998 | |
| JP | 2001131866 A | | 5/2001 | |
| JP | 2005119967 | | 5/2005 | |
| JP | 2005306742 A | | 11/2005 | |
| JP | 2006050934 A | | 2/2006 | |
| JP | 2006246817 A | | 9/2006 | |
| JP | 2006249599 A | | 9/2006 | |
| JP | 2006256968 A | | 9/2006 | |
| JP | 2007098152 | | 4/2007 | |
| JP | 2008274535 A | | 11/2008 | |
| JP | 2011182783 A | | 9/2011 | |
| KR | 20070090286 A | * | 9/2007 | |
| KR | 20100114348 | | 10/2010 | |
| WO | WO9409653 | | 5/1994 | |
| WO | WO 0205655 | | 1/2002 | |
| WO | WO03091500 | | 11/2003 | |

OTHER PUBLICATIONS

Raventos et al., Application and Possibilities of Supercritical $CO_2$ Extraction in Food Processing Industry: An Overview, Food Science Tech. Int. (2002) vol. 8 (5) pp. 269-284.

Greer, C.C,. A Text-Book of Cooking; J.S. Cushing Co.—Berwick & Smith Co. Norwood, MA 1915, pp. 175-177.

(56) References Cited

OTHER PUBLICATIONS

Innovation Food Online, Sodium Alginate; URL<https://innovationintood.wikispaces.com/Sodium+alginate> Published Jan. 4, 2007 Online, 7 pages with one extra page having google search hit with datestamp.

CN20080097787; Huimin. Y., dated Apr. 2009, English Abstract Only, 2 pages.

SU1161061; Choladze, et al. dated Jun. 1985, English Abstract Only, 2 pages.

Blumenthal et al., Herbal Medicine, Expanded Commission E. Monographs, 2000, pp. 393-400.

Adams et al., Analysis of the Interactions of Botanical Extract Combinations Against the Viability of Prostate Cancer Ceil Lines. Mar. 2003, pp. 117-124.

Lin et al., Inhibition of Helicobacter Pylon and Associated Urease by Oregano and Cranberry Phytochemical Synergies, Applied and Environmental Microbiology, Dec. 2005, vol. 71., No. 12, pp. 8558-8564.

Co-pending U.S. Appl. No. 15/053,134, dated Feb. 25, 2016.

\* cited by examiner

COMPOSITION FOR MAKING A TEA BEVERAGE OR HERBAL AND VEGETABLE BROTHS

RELATED APPLICATIONS

The present application is a continuation-in-part application of U.S. patent application Ser. No. 14/193,910, filed on Feb. 28, 2014, which is incorporated herein by reference. The present application is also based upon and claims priority to U.S. Provisional Patent Application Ser. No. 61/770,564 filed on Feb. 28, 2013, which is incorporated herein by reference.

FIELD OF THE INVENTION

The present invention relates to an infusion product for making a beverage, more specifically to a plant-based composition for making a beverage, and to a herbal and/or vegetable composition or bouquet garni, for food, medicinal or aromatic applications. The plants (raw materials) are fruits, herbs, medicinal plants, tea, vegetables and/or spices. The invention further relates to a method for producing said compositions or infusion product, its use for making a (tea) beverage, and a (tea) beverage so obtained. Further, the present invention relates to a fiber-web, preferably a tea bag, made from said fruits, herbs, medicinal plants, tea, vegetable and/or spices.

BACKGROUND OF THE INVENTION

A quick cup of tea, either from herbs, medicinal plants or tea plants (*Camellia sinensis*), also called "infusion" or "tisane" may be produced by putting conventional tea bags filled with parts of said fruits, herbs, medicinal plants, or tea (such as, for example, in the form of leaves or powder) in a cup of hot or boiling water. For some teas, such as fruit teas or teas made from herbs or medicinal plants, the steep time is rather long, whereas for various kinds of tea plants, maintaining a certain steep time is required for producing the best flavour. In some cases, there is either an incomplete extraction from the bag, resulting in a highly variable and generally weak flavored beverage, or an excessive extraction, resulting in a highly variable and generally strong or even bitter taste. The flavour and taste also greatly depends on water quality and temperature.

Similarly, herbs and spices are used for cooking, for example in a loose form or as a bouquet garni, or in the form of powders or bouillon cubes. However, broth made from rehydrated cubes is different in taste from fresh broth because of its higher salt content and flavours changed by the boiling process. Bouillon cubes are convenient and inexpensive but have little nutritive value.

There is still a need to improve infusion products for making a tea beverage, in particular to allow for fast infusion that is more independent from external factors and temperature and suitable to provide a more standardized beverage or herb-infused broth while avoiding variable infusion results.

SUMMARY OF THE INVENTION

In one embodiment of the present invention, a composition for making a beverage is provided, the composition comprising a layer of fibrous plant product and a plant extract applied thereto. In another embodiment of the present invention, a herbal and/or vegetable composition or bouquet garni is provided, also referred to as herbal infusion or herb-infused broth products, wherein the herbal and/or vegetable composition comprises a layer of fibrous plant product and a plant extract applied thereto.

In the products of the invention, the plant is for example selected from the group consisting of fruits, herbs, medicinal plants, tea, vegetables and spices, including mixtures thereof, such as, for example, mixtures of herbs, vegetables and/or spices.

A further embodiment of the invention relates to a method for producing the composition of the present invention. For example, the method comprises the steps of:
a) extracting components of at least one plant with a solvent;
b) separating the soluble portion (plant extract) from the non-soluble portion (solid plant particles);
c) optionally refining the non-soluble portion;
d) preparing a sheet-like product from the non-soluble portion;
e) optionally concentrating the soluble portion;
f) applying the soluble portion of step b) or concentrated soluble portion of step e) to the sheet of step d); and
g) drying the product of step f) to obtain the composition of the invention.

In a further embodiment, the invention relates to a fiber-web comprising from about 5% to about 100% (w/w), preferably at least 10%, at least 20%, at least 30%, at least 40%, at least 50%, at least 60%, at least 70%, at least 80%, at least 90%, or 100%, fibers of fruits, herbs, medicinal plants, tea, vegetables and/or spices. In one embodiment, the fiber-web further comprises (i) fibers of fruits, herbs, medicinal plants, tea, vegetables and/or spices, and (ii) cellulosic and/or synthetic fibers in a ratio of for example: 40/60 (w/w), 60/40 (w/w) or 20/80 (w/w). In another embodiment of the invention, the fiber-web of the present invention is obtainable by the method disclosed herein, namely as an intermediate product in step d) of the said method.

According to a further embodiment, the fiber-web of the invention further comprises a coating or an impregnation with the soluble portion (plant extract) of said fruits, herbs, medicinal plants, or tea. In another embodiment of the invention, the fiber-web of the present invention is obtainable by the method disclosed herein, namely as the end product in step g) of said method.

In a further embodiment, the invention relates to a tea bag comprising the fiber-web referred to herein, which is either impregnated with the soluble portion (plant extract) of said fruits, herbs, medicinal plants, or tea, or which is not impregnated. The tea bag may be empty or filled i.e. the tea bag may further comprise inside a sample or portion of fruits, herbs, medicinal plants, or tea.

Various different products can be made in accordance with the present disclosure for producing a beverage or broth. For instance, in one embodiment, the product comprises a dispenser defining an opening. An infusion product comprising a strip made from a layer of fibrous plant material is contained within the dispenser and dispensed through the opening. The infusion product is configured to produce a beverage or broth when contacted with a liquid. For instance, the fibrous plant material may comprise a tea that has been treated with a plant extract. The plant extract can also comprise a tea. In this manner, the strip made from the layer of fibrous plant material can be used to produce a tea product.

In one embodiment, the infusion product comprises a single continuous strip contained within the dispenser. For instance, the infusion product can be spirally wound within the dispenser. The infusion product can include periodic perforation lines that extend across the width of the strip. In this manner, a user can tear the strip along the perforation lines when the product is being dispensed. Alternatively, the dispenser can include a cutting device, such as a serrated edge, for dispensing the product.

In an alternative embodiment, the infusion product comprises a plurality of individual strips contained within the dispenser. The individual strips can be connected together or can be contained in the dispenser as separate and discrete strips. In one embodiment, each individual strip can include a tab portion for holding the strip during use. The tab portion can comprise a coating applied to the strip made from the layer of fibrous plant material or can comprise a different material that is laminated to the strip or otherwise attached to the strip. In one embodiment, the tab portion can comprise an adhesive portion that contains an adhesive material. The adhesive portion is for adhering the infusion product to an adjacent surface, such as the edge of a cup or mug. In one embodiment, the adhesive portion can further include a release liner that covers the adhesive material prior to use.

In an alternative embodiment, the infusion product comprises a cylindrical member comprising a reconstituted material. The reconstituted material comprises a fibrous plant product that has been treated with a plant extract. The fibrous plant product, for instance, may contain a plant material comprising a fruit, an herb, a medicinal plant, a tea, a vegetable, a spice, or mixtures thereof. In one embodiment, the reconstituted material comprises 70% by weight of a tea.

In one embodiment, the cylindrical member may comprise a straw that includes a top and a bottom and that defines a hollow passageway that extends from the top to the bottom. The straw can be constructed by spirally winding together a sheet of the reconstituted material. When contacted with a liquid, the cylindrical member or straw can be used to produce a broth or beverage. The cylindrical member or straw can also be used to stir the beverage.

In still another embodiment, the present disclosure is directed to a product for producing a broth or beverage and comprises a sealed capsule having a top. The sealed capsule defines a single chamber. The single chamber contains a reconstituted material in accordance with the present disclosure. The reconstituted material comprises a fibrous plant product that has been treated with a plant extract. The fibrous plant product comprises a tea.

In still another embodiment, the infusion product of the present disclosure comprises a shaft member connected to or integral with a plurality of infusion filaments. A sliding member is present on the shaft member that can slide over the infusion filaments and protect them prior to use. During use, the sliding member can be slid over the shaft member exposing the infusion filaments for contact with a liquid, such as water. In one embodiment, the shaft member and the infusion filaments can all be made from a reconstituted material. Alternatively, the infusion filaments may comprise strips, ribbons, fibers, rods, or the like that are attached to the shaft member. In this embodiment, the shaft member can be made from any suitable material, such as a paper product, a plastic product, or the like. The shaft member and sliding member can be used to hold the infusion product and assist in stirring the product when the infusion filaments are contacted with water in order to produce a broth or beverage.

In still another embodiment, the infusion product comprises a layer of fibrous plant product that has been treated with a plant extract. In one embodiment, for instance, the fibrous plant product and plant extract comprise tea. The layer of fibrous plant product can be in the form of a rectangular or square strip and can include a reinforced area. The reinforced area can be produced by laminating to the layer of fibrous plant product one or more layers of a reinforcing material. The reinforced area can define an opening for receiving a rod member. The opening, for instance, can be an aperature, a slot, a channel, or the like. During use, a rod member is inserted through the opening such that the layer of fibrous plant product hangs from the rod member. The rod member can then be placed over the opening of a container, such as a cup or mug for holding the infusion product while the product is being contacted with a liquid in producing a beverage or broth. In one embodiment, the rod member can also be made from a reconstituted material. In this manner, the rod member can be used not only to stir the beverage but also to further add flavor. When made from a reconstituted material, the rod member can include a handle portion. The rod member can have a straight linear shape or can have a curved shape. In one embodiment, the rod member is in the shape of a ring. The ring can define an opening for fitting over the edge of a cup.

In still another embodiment, the infusion product of the present disclosure comprises a lining. The lining can have a shape configured to fit any suitable container. In one embodiment, for instance, the lining can be configured to fit into a cup. The lining can be made from the reconstituted material comprising a layer of fibrous plant product that has been treated with a plant extract.

In one embodiment, the lining can be a separate article placed into a cup or other container. Alternatively, the lining can be made so as to be integral with the cup or container. For instance, the cup itself can be made from the reconstituted material or the layer of fibrous plant product can be connected to or otherwise laminated to the material used to form the cup.

In still another embodiment, the infusion product of the present disclosure comprises an infusion member attached to a cap member. The infusion member can be made from the reconstituted material of the present disclosure. For instance, the infusion member can be made from a fibrous plant product that has been treated with a plant extract. In one embodiment, the fibrous plant product comprises a tea for producing a tea beverage.

The infusion member can have any suitable shape. For instance, the infusion member may comprise a rod, a tube, a column, a pillar, a plurality of filaments or the like.

As described above, the infusion member is connected to a cap member. The cap member can include threads for engaging the threads on a bottle. In one embodiment, for instance, the cap member is designed to form a liquid tight fit on a water bottle. In this embodiment, when producing a beverage, the infusion member can be placed into the water bottle so as to contact the liquid therein. The cap member can then be screwed onto the water bottle or otherwise attached. The water bottle can then be shaken so that a beverage is produced through contact between the water and the infusion member.

In yet another embodiment of the present disclosure, the infusion product comprises a cup or tumbler having a top that forms a liquid tight fit with the cup or tumbler. An infusion member can be placed within the cup or tumbler. In one embodiment, for instance, the infusion member has a disk-like shape that matches and is smaller than the inside diameter of the cup or tumbler. In this manner, the infusion member can be placed at the bottom of the cup or tumbler.

The infusion product can also include a baffle. The baffle can have a diameter or dimensions that substantially match the inside diameter or dimensions of the cup or tumbler. The baffle can be placed inside the cup or tumbler and used to cover the infusion member. In one embodiment, the baffle comprises a perforated base.

In order to produce a beverage, the infusion member is placed inside the cup or tumbler, the baffle is then placed over the infusion member within the cup or tumbler. The cup or tumbler is then filled with a liquid, such as water, and the top is placed on the cup or tumbler. Once a top is placed on the cup or tumbler, the entire product can be shaken in order to produce a beverage.

In all of the embodiments described above, the reconstituted material can be used to produce a tea or herbal tea product. Each of the reconstituted materials described above, for instance, may comprise tea or herbal tea plants in an amount of at least 70% by weight. In addition, the extract applied to the fibrous material can also contain tea plant or herbal plant materials in an amount of at least 70% by weight.

DETAILED DESCRIPTION OF THE INVENTION

Figure 1:
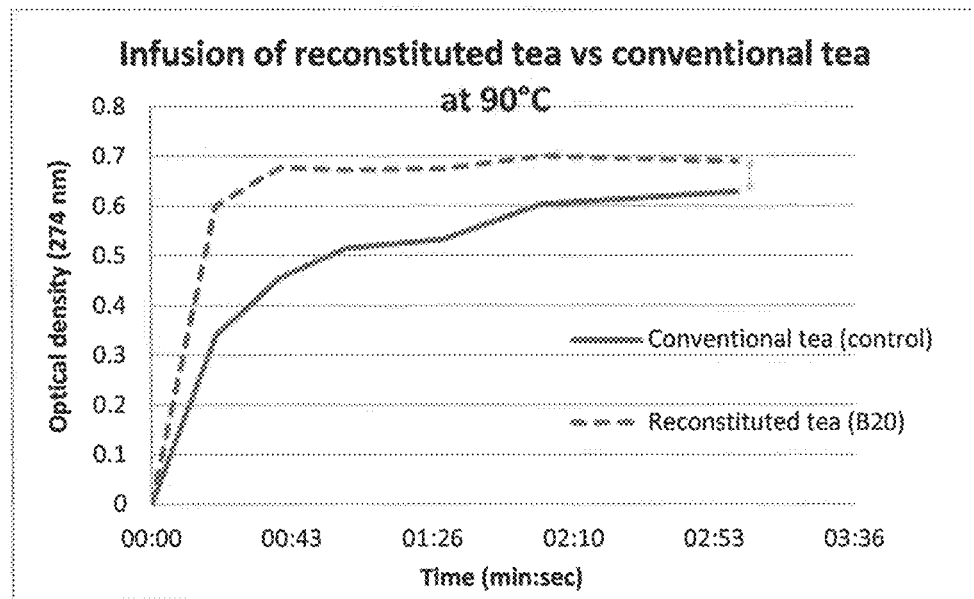
FIG. 1 is a graph showing total infusion time in hot water (90° C.) for an impregnated tea product (fiber-web made of non soluble tea particles impregnated with soluble tea portion) as compared to a conventional tea in the form of a tea bag.

In one embodiment of the present invention, a composition for making a beverage (such as a drink or tea) is provided, the composition comprising a layer of fibrous plant product and a plant extract applied thereto. In another embodiment of the present invention, a herbal, vegetable and/or spice composition or bouquet garni is provided, the composition comprising a layer of fibrous plant product and a plant extract applied thereto. The composition is a plant-based composition or product which is also referred to as plant composition or infusion product, respectively. Hereinafter, the aforementioned compositions are often referred to as "composition(s) or product(s) of the invention", "composition(s)" or "products". The herbal, vegetable and/or spice composition or bouquet garni is also referred to as "mixture of herbs and spices", "herbal infusion" or "herb-infused broth product". These terms are used interchangeably and are not intended to limit the invention.

As used herein, the term "plant" likewise refers to any living organism of the kingdom Plantae and includes plants described as grains, fruits and vegetables as well as plant parts, such as roots, barks, seeds, stems, leaves, flowers and fruits.

In the products of the invention, the plant is for example selected from the group consisting of fruits, herbs, medicinal plants, tea, vegetables and/or spices, including mixtures thereof, such as mixtures of herbs and vegetables, or herbs and spices.

As used herein, a spice is a dried seed, fruit, root, bark, or vegetative substance primarily used for flavoring, coloring or preserving food. As used herein, herbs are any plants used for flavoring, food, medicine, or perfume. Culinary use typically distinguishes herbs as referring to the leafy green parts of a plant (either fresh or dried), from a "spice", a product from another part of the plant (usually dried), including seeds, berries, bark, roots and fruits.

In connection with the present invention, the term "planthowever, any plant part may be utilizes, such as roots, bark, seeds, stems, leaves, flowers and fruit.

The fruits, herbs, medicinal plants, tea, vegetables and spices are for example selected from artemisia, balm, basil, chamomile, chive, cloves, coffee, coriander, dill, garlic, ginger, ginseng, gingko, jasmine, lavender, mint, orange blossom, oregano, persil, rooibos, rosa centifolia, rosemary, thyme, turmeric, sage, pepper, chili pepper, Stevia Rebaudiana, tarragon, white tea, yellow tea, green tea, oolong tea, black tea, pu-erh tea, vanilla, red or green vine, violet and/or willow.

In some embodiments of the invention, the plant is for example selected from the group consisting of culinary herbs and spices such as:

Ajwain, carom seeds (*Trachyspermum ammi*), Akudjura (*Solanum centrale*), Alexanders (*Smyrnium olusatrum*), Alkanet (*Alkanna tinctoria*), Alligator pepper, mbongo spice (mbongochobi), hopper pepper (*Aframomum danielli, A. citratum, A. exscapum*), Allspice (*Pimenta dioica*), *Angelica* (*Angelica archangelica*), Anise (*Pimpinella anisum*), Aniseed myrtle (*Syzygium anisatum*), Annatto (*Bixa orellana*), Apple mint (*Mentha suaveolens*), Asafoetida (*Ferula assafoetida*), Asarabacca (*Asarum europaeum*), Avens (*Geum urbanum*), Avocado leaf (*Peresea americana*), Barberry (*Berberis vulgaris* and other *Berberis* spp.), Basil, sweet (*Ocimum basilicum*), Basil, lemon (*Ocimum×citriodorum*), Basil, Thai (*O. basilicum* var, *thyrsiflora*), Basil, Holy (*Ocimum tenuiflorum*), Bay leaf (*Laurus nobilis*), Bay leaf; Indian, tejpat, malabathrum, Boldo (*Peumus boldus*), Borage (*Borago officinalis*), Black cardamom (*Amomum subulatum, Amonium costatum*), Black mustard (*Brassica nigra*), Blue fenugreek, blue melilot (*Trigonella caerulea*), Brown mustard (*Brassica juncea*), Caraway (*Carum carvi*), Cardamom (*Elettaria cardamomum*), Carob (*Ceratonia siliqua*), Catnip (*Nepeta cataria*), Cassia (*Cinnamomum aromaticum*), Cayenne pepper (*Capsicum annuum*), Celery leaf (*Apium graveolens*), Celery seed (*Apium graveolens*), Chervil (*Anthriscus cerefolium*), Chicory (*Cichorium intybus*), Chili pepper (*Capsicum* spp.), Chives (*Allium schoenopasum*), Cicely, sweet cicely (*Myrrhis odorata*), Cilantro, coriander greens, coriander herb (*Coriandrum sativum*), Cinnamon, Indonesian (*Cinnamomum burmannii, Cassia vera*), Cinnamon, Saigon or Vietnamese (*Cinnamomum loureiroi*), Cinnamon, true or Ceylon (*Cinnamomum verum, C. zeylanicum*), Cinnamon, white (*Canella winterana*), Cinnamon myrtle (*Backhousia myrtifolia*), Clary, Clary sage (*Salvia sclarea*), Clove (*Syzygium aromaticum*), Coriander seed (*Coriandrum sativum*), Costmary (*Tanacetum balsamita*), Cuban oregano (*Plectranthus amboinicus*), Cubeb pepper (*Piper cubeba*), Cudweed (*Gnaphalium* spp), Culantro, culangot, long coriander (*Eryngium foetidum*), Cumin (*Cuminum cyminum*), Curry leaf (*Murraya koenigii*), Curry plant (*Helichrysum italicum*), Dill seed (*Anethum graveolens*), Dill herb or weed (*Anethum graveolens*), Elderflower (*Sambucus* spp.), Epazote (*Dysphania ambrosioides*), Fennel (*Foeniculum vulgare*), Fenugreek (*Trigonella foenum-graecum*), Filé powder, gumbo filé (*Sassafras albidum*), Fingerroot, *krachai, temu kuntji* (*Boesenbergia rotunda*), Galangal, greater (*Alpinia galanga*), Galangal, lesser (*Alpinia officinarum*), Galingale (*Cyperus* spp.), Garlic chives (*Allium tuberosum*), Garlic (*Allium sativum*), Garlic, elephant (*Allium ampeloprasum* var. *ampeloprasum*), Ginger (*Zingiber officinale*), Ginger, torch, *bunga siantan* (*Etlingera elatior*) (Indonesia), *Golpar*, Persian hogweed (*Heracleum persicum*) (Iran), Grains of paradise (*Aframomum melegueta*), Grains of Selim, Kani pepper (*Xylopia aethiopica*), Horseradish (*Armoracia rusticana*), *Houttuynia cordata* (Vietnam), Huacatay, Mexican marigold, mint marigold (*Tagetes minuta*), Hyssop (*Hyssopus officinalis*), Indonesian bay leaf, *daun salam* (*Syzygium polyanthum*), Jasmine flowers (*Jasminum* spp.), Jimbu (*Allium hypsistum*) (Nepal), Juniper berry (*Juniperus communis*), Kaffir lime leaves, Makrud lime leaves (*Citrus hystrix*) (Southeast Asia), Kala zeera (or kala jira), black cumin (*Bunium persicum*) (South Asia), Kawakawa seeds (*Macropiper excelsum*) (New Zealand), *Kencur, galangal, keptjur* (*Kaempferia galanga*), Keluak, kluwak, kepayang (*Pangium edule*), *Kinh gioi*, Vietnamese balm (*Elsholtzia ciliata*), *Kokam* seed (*Garcinia indica*) (Indian confectionery), *Korarima*, Ethiopian cardamom, false cardamom (*Aframomum corrorima*) (Eritrea), *Koseret* leaves (*Lippia adoensis*) (Ethiopia), Lavender (*Lavandula* spp.), Lemon balm (*Melissa officinalis*), Lemongrass (*Cymbopogon citratus, C. flexuosus*, and other *Cymbopogon* spp.), Lemon ironbark (*Eucalyptus staigeriana*) (Australia), Lemon myrtle (*Backhousia citriodora*) (Australia), Lemon verbena (*Lippia citriodora*), Leptotes bicolor (Paraguay and southern Brazil), Lesser calamint (*Calamintha nepeta*), *nipitella, nepitella* (Italy), Licorice, liquorice (*Glycyrrhiza glabra*), Lime flower, linden flower (*Tilia* spp.), Lovage (*Levisticum officinale*), Mace (*Myristica fragrans*), *Mahlab*, St. Lucie cherry (*Prunus mahaleb*), Marjoram (*Origanum maforana*), Marsh mallow (*Althaea officinalis*), Mastic (*Pistacia lentiscus*), Mint (*Mentha* spp.) 25 species, hundreds of varieties, Mountain horopito (*Pseudowintera colorata*) 'Pepperplant' (New Zealand), Musk mallow, *abelmosk* (*Abelmoschus moschatus*), Mustard, black, mustard plant, mustard seed (*Brassica nigra*), Mustard, brown, mustard plant, mustard seed (*Brassica juncea*), Mustard, white, mustard plant, mustard seed (*Sinapis alba*), Nasturtium (*Tropaeolum majus*), Nigella, kalonji, black caraway, black onion seed (*Nigella sativa*) Njangsa, djansang (*Ricinodendron heudelotii*) (West Africa), Nutmeg (*Myristica fragrans*), Neem, Olida (*Eucalyptus olida*) (Australia), Oregano (*Origanum vulgare, O. heracleoticum*, and other species), Orris root (*Iris germanica, I. florentina, I. pallida*), Pandan flower, *kewra* (*Pandanus odoratissimus*), Pandan leaf, screwpine (*Pandanus amaryllifolius*, Paprika (*Capsicum annuum*), Paracress (*Spilanthes acmella, Soleracea*) (Brazil), Parsley (*Petroselinum crispum*), Pepper: black, white, and green (*Piper nigrum*), Pepper, Dorrigo (*Tasmannia stipitata*) (Australia), Pepper, long (*Piper longum*), Pepper, mountain, Cornish pepper leaf (*Tasmannia lanceolata*), Peppermint (*Mentha piperata*), Peppermint gum leaf (*Eucalyptus dives*), *Perilla, shiso* (*Perilla* spp.), Peruvian pepper (*Schinus molle*), *Pandanus amaryllifolius*, Brazilian pepper or Pink pepper (*Schinus terebinthifolius*), Quassia (*Quassia amara*) (bitter spice in aperitifs and some beers and fortified wines), Ramsons, wood garlic (*Allium ursinum*), Rice paddy herb (*Limnophila aromatica*) (Vietnam), Rosemary (*Rosmarinus officinalis*) Rue (*Ruta graveolens*), Safflower (*Carthamus tinctorius*), for yellow color, Saffron (*Crocus sativus*), Sage (*Salvia officinalis*), Saigon cinnamon (*Cinnamomum loureiroi*), Salad burnet (*Sanguisorba minor*), Salep (*Orchis mascula*), Sassafras (*Sassafras albidum*), Savory, summer (*Satureja hortensis*), Savory, winter (*Satureja montana*), Silphium, silphion, laser, laserpicium, lasarpicium (Ancient Roman cuisine, Ancient Greek cuisine), *Shiso* (*Perilla frutescens*), Sorrel (*Rumex acetosa*), Sorrel, sheep (*Rumex acetosella*), Spearmint (*Mentha spicata*), Spikenard (*Nardostachys grandiflora* or *N. jatamansi*), Star anise (*Illicium verum*), Sumac (*Rhus coriaria*), Sweet woodruff (*Galium odoratum*), Szechuan pepper, Sichuan pepper (*Zanthoxylum piperitum*), Tarragon (*Artemisia dracunculus*), Thyme (*Thymus vulgaris*), Thyme, lemon (*Thymus×citriodorus*), Turmeric (*Curcuma longa*), Vanilla (*Vanilla planifolia*), Vietnamese cinnamon (*Cinnamomum loureiroi*), Vietnamese coriander (*Persicaria odorata*), Voatsiperifery (*Piper borbonense*), Wasabi (*Wasabia japonica*), Waterpepper, smartweed (*Polygonum hydropiper*), Watercress (*Rorippa nasturtium-aquatica*), Wattleseed (from about 120 spp, of Australian *Acacia*), White mustard (*Sinapis alba*), Wild betel (*Piper sarmentosum*) (Southeast Asia), Wild thyme (*Thymus serpyllum*), Willow herb (*Epilobium parviflorum*), Winter savory (*Satureja montana*), Wintergreen (*Gaultheria procumbens*), Wood awns, herb bennet (*Geum urbanum*), Woodruff (*Galium odoratum*), Wormwood, absinthe (*Artemisia absinthium*), Yellow mustard (*Brassica hirta*=*Sinapis alba*), Yerba buena. any of four different species, many unrelated, Za'atar (herbs from the genera *Origanum, Calamintha, Thymus*, and/or *Satureja*), Zedoary (*Curcuma zedoaria*).

In some embodiments of the invention, the plant is selected from the group consisting of teas and herbal teas such as:

Anise tea (seeds or leaves), Asiatic penny-wart leaf, Artichoke tea, Bee Balm, Boldo, Burdock, Caraway tea, Catnip tea, Chamomile tea, Che Dang tea (*Ilex causue* leaves), Chinese knot-weed tea, Chrysanthemum tea, Cinnamon, Coca tea, Coffee tea leaves and coffee cherry tea, Cerasse, Citrus peel (including bergamot, lemon and orange peel), Dandelion coffee, Dill tea, Echinacea tea, Elderberry, European Mistletoe (*Viscum album*), Essiac tea, Fennel, Gentian, Ginger root, Ginseng, Goji, Hawthorn, Hibiscus, Ho Yan Hor Herbal Tea, Honeybush, Horehound, Houttuynia, Hydrangea tea (*Hydrangea serrata* Amacha), Jiaogulan, Kapor tea, Kava root, Kratom, Kuzuyu, Labrador tea, Lapacho (also known as *Taheebo*), Lemon Balm, Lemon and ginger tea, Lemon grass, Luo han guo, Licorice root, Lime blossom, Mint, Mountain Tea, Neem leaf, Nettle leaf, New Jersey Tea, Noni tea, Oksusu cha, Pennyroyal leaf, Pine tea, Qishr, Red clover tea, Red raspberry leaf, Roasted barley tea, Roasted wheat, Rooibos (Red Bush), Rose hip, Roselle petals (species of Hibiscus; aka Bissap, Dah, etc.), Rosemary, Sagebrush, California Sagebrush, Sage, Sakurayu, Salvia, Scorched rice, Skullcap, Serendib (tea), Sohacha, Spicebush (Lindera benzoin), Spruce tea, Staghorn sumac fruit, Stevia, St. John's Wort, Tea (*Camellia sinensis*) Thyme, Tulsi, Holy Basil, *Uncaria tomentosa*, commonly known as Cat's Claw, Valerian, Verbena (Vervains), Vetiver, Wax gourd, Wong Lo Kat, Woodruff, and/or Yarrow.

In some embodiments of the invention, the plant is for example selected from the group consisting of medicinal plants such as:

Açai (*Euterpe oleracea*, Alfalfa (*Medicago sativa*), Arnica (*Arnica Montana*, Asthma weed (*Euphorbia hirta*), Astragalus (*Astragalus propinquus*), Barberry (*Berberis vulgaris*), Belladonna (*Atopa belladonna*, Bilberry (*Vaccinium myrtillus*), Bitter gourd (*Momordica charantia*), Bitter leaf (*Vernonia amygdalina*), Bitter orange (*Citrus*×*aurantium*), Black cohosh (*Actaea racemosa*), Blessed thistle (*Cnicus benedictus*), Blueberries (genus *annuum*), Burdock (*Arctium lappa*), Cat's claw (*Uncaria tomentosa*), Cayenne (*Capsicum annuum*), Celery (*Apium graveolens*), Chamomille (*Matricaria recutita* and *Anthemis nobilis*), Chaparral (*Larrea tridentata*), Chasteberry (*Vitex agnus-castus*), Chili (*Capsicum frutescens*), Cinchona, Clove (*Syzygium aromaticum*), Coffee senna (*Cassia occidentalis*), Comfrey (*Symphytum officinale*), Cranberry (*Vaccinium macrocarpon*), Dandelion (*Taraxacum officinale*), Dong quai (*Angelica sinensis*), Elderberry (*Sambucus nigra*), Eucalyptus (*Eucalyptus globulus*), European Mistletoe (*Viscum album*), Evening primrose (*Oenothera* spp.), Fenugreek (*Trigonella foenum-graecum*), Feverfew (*Tanacetum parthenium*), Flaxseed (*Linum usitatissimum*), Garlic (*Allium sativum*), Ginger (*Zingiber officinale*), Gingko (*Gingko biloba*), Ginseng (*Panax ginseng* and *Panax quinquefolius*), Goldenseal (*Hydrastis canadensis*) Grape (*Vitis vinifera*) Guava (*Psidium guajava*), Hawthorn (specifically *Crataegus monogyna* and *Crataegus laevigata*), Hoodia (*Hoodia gordonii*), Horse chestnut (*Aesculus hippocastanum*), Horsetail (*Equisetum arvense*), Jamaica dogwood (*Piscidia erythrina* or *Piscidia piscipula*), Kava (*Piper methysticum*), Kha Konjac (*Amorphophallus konjac*), Kratom (*Mitragyna speciosa*), Kanna (*Sceletium tortuosum*), Lavender (*Lavandula angustifolia*), Lemon (*Citrus limon*), Licorice root (*Glycyrrhiza glabra*), Marigold (*Calendula officinalis*), Marsh mallow (*Althaea officinalis*), Milk thistle (*Silybum marianum*), Neem (*Azadirachta indica*), Noni (*Morinda citrifolia*), Oregano (*Origanum vulgare*), Papaya (*Carica papaya*), Peppermint (*Mentha*×*piperita*) Purple coneflower (*Echinacea purpurea*), Passion Flower (*Passiflora*), Red clover (*Trifolium pratense*), Rosemary (*Rosmarinus officinalis*) Sage (*Salvia officinalis*), Syrian Rue (aka Harmal) (*Peganum harmala*), St. John's wort (*Hypericum perforatum*), Saw palmetto (*Serenoa repens*), Thunder God Vine (*Tripterygium wilfordii*), Thyme (*Thymus vulgaris*), Tulasi (*Ocimum tenuiflorum* or Holy Basil), Turmeric (*Curcuma longa*), Umckaloabo (*Pelargonium sidoides*), Valerian (*Valeriana officinalis*), White willow (*Salix alba*), and/or Yerba santa (*Eriodictyon crassifolium*).

As disclosed herin, mixtures of the above-mentioned culinary, herbal and/or medicinal plants are also included as part of the invention.

In a preferred embodiment of the invention, the plant is tea (*Camellia sinensis*), including white tea, yellow tea, green tea, oolong tea, black tea, and/or pu-erh tea, and the like, including mixtures or blends thereof.

In one embodiment, the composition of the invention (either for making a drink or as a mixture of herbs and spices) comprises a layer of fibrous plant product, wherein the fibrous plant product comprises a blend of different plants.

In one embodiment, the composition of the invention (either for making a drink or as a mixture of herbs and spices) comprises a plant extract, wherein the plant extract comprises a blend of different plants.

In another embodiment, the composition comprises a layer of fibrous plant product and a plant extract applied thereto, wherein the fibrous plant product comprises a blend of different plants and the plant extract comprises a blend of different plants, or wherein the fibrous plant product comprises a single plant and the plant extract comprises a blend of different plants, or wherein the fibrous plant product comprises a blend of different plants and the plant extract comprises a single plant.

In another embodiment of the composition, the layer of fibrous plant product and the plant extract are from the same plant or from different plants.

In one embodiment of the invention, the layer of fibrous plant product of the composition comprises at least 70% (w/w) of fibrous plant product from one plant.

In one embodiment of the invention, the plant extract comprises at least 70% (w/w) of a plant extract from one plant. In another embodiment, the composition comprises at least 70% of fibrous plant product, preferably where the at least 70% of a plant extract is from tea.

The herbal and/or vegetable composition is preferably a composition for culinary use or for use in cooking, i.e. as a herb and spice mixture instead of a conventional bouquet garni.

A conventional bouquet garni is a bundle of herbs usually tied together with string and mainly used to prepare soup, stock, and various stews (herb and spice mixture). The bouquet is cooked with the other ingredients but is removed prior to consumption. Sometimes, the bouquet garni is not bound with string but its ingredients are filled into a small sachet, a net, or even a tea strainer, instead. Traditionally, the aromatics are bound within leek leaves, though a coffee filter (or cheesecloth) and butcher twine can be used, instead.

The herbal and/or vegetable composition or bouquet garni of the invention may be used instead of a traditional bouquet garni. The herbal and/or vegetable composition or bouquet garni of the invention is either made from a single herb or vegetable (such as parsley, thyme, bay leaf, basil, burnet, chervil, rosemary, peppercorns, savory and tarragon, carrot, celery (leaves or stem), celeriac, leek, onion and parsley root) or from a mixture of herbs and/or vegetables. If a mixture of herbs and/or vegetables is used, the composition may be used as a new form of a bouquet garni ("garnished bouquet"). In one embodiment, the herbs for the bouquet garni of the invention are parsley, thyme and bay leaf, in another embodiment, and depending on the recipe, the bouquet garni may also include basil, burnet, chervil, rosemary, peppercorns, savory and tarragon. Vegetables such as carrot, celery (leaves or stem), celeriac, leek, onion and parsley root are sometimes included in the bouquet garni of the invention.

A further embodiment of the invention relates to a method for producing the composition for making a beverage of the present invention. For example, the method comprises the steps of:
a) extracting components of at least one plant with a solvent;
b) separating the soluble portion (plant extract) from the non-soluble portion (solid plant particles);
c) optionally refining the non-soluble portion;
d) preparing a sheet-like product from the non-soluble portion;
e) optionally concentrating the soluble portion;
f) applying the soluble portion of step b) or concentrated soluble portion of step e) to the sheet of step d); and
g) drying the product of step f) to obtain the composition for making a beverage.

In one embodiment of the invention, one or more plant components (plant material or plant funish) such as, for example, stems, scraps, leaves, fines, dust and/or shorts, are initially mixed with a solvent (e.g., water and/or other compounds) at elevated temperatures. For example, various solvents that are water-miscible, such as alcohols (e.g., ethanol), can be combined with water to form an aqueous solvent. The water content of the aqueous solvent can, in some instances, be greater than 50% by weight of the solvent. In one embodiment, the water content is 70%, 80%, 90% or 100%. Deionized water, distilled water or tap water may be employed. The amount of the solvent in the suspension can vary widely, but is generally added in an amount from about 75% to about 99% by weight of the suspension. However, the amount of solvent can vary with the nature of the solvent, the temperature at which the extraction is to be carried out, and the type of plant components.

After forming the solvent/plant furnish mixture, some or all of a soluble extracts fraction of the furnish mixture may be optionally separated (e.g., extracted) from the mixture. If desired, the aqueous solvent/plant furnish mixture can be agitated during extraction by stirring, shaking or otherwise mixing the mixture in order to increase the rate of extraction. Typically, extraction is carried out for about 0.5 hours to about 6 hours. Moreover, although not required, typical extraction temperatures range from about 10° C. to about 100° C.

Prior to the extraction step an optional grinding or cutting step can be used, in order to shred the plant or plant part and thus to break the plant's cell walls.

Once separated from the insoluble residue fraction of the plant solution, the soluble extracts fraction can optionally be concentrated using any known type of concentrator, such as a vacuum evaporator. In one embodiment, the soluble component may be highly concentrated. Moreover, the concentrated or unconcentrated soluble extracts fraction can be utilized in any manner desired. For example, the soluble extracts fraction can be utilized as a flavouring material or a portion can be added to the insoluble residue fraction.

Once extracted, the insoluble residue fraction can optionally be subjected to one or more mechanical refiners to produce a fibrous pulp. Some examples of suitable refiners can include disc refiners, conical refiners, and the like. The insoluble residue fraction can be utilized in any manner desired. For example, the insoluble residue fraction can be used as a flavouring material, used to produce a composition of the invention, which is herein also referred to as reconstituted plant material.

To produce a composition of the invention, the insoluble residue fraction is transferred to a papermaking station. The papermaking station includes a forming apparatus, which may include, for example, a forming wire, gravity drain, suction drain, felt press, Yankee dryer, drum dryers, etc. In general, the insoluble residue fraction may be in the form of a pulp. In the forming apparatus, the pulp is laid onto a wire belt forming a sheet-like shape. Excess water is removed from the tobacco sheet using gravity drains, suction drains, presses, and dryers. Thereafter, if desired, a portion of the soluble extracts fraction may be reapplied to the insoluble residue fraction. When the insoluble residue fraction is recombined with the soluble extracts fraction, the resulting plant product is generally referred to as "reconstituted plant material."

Reconstituted plant material can generally be formed in a variety of ways. For instance, in one embodiment, band casting can be utilized to form the reconstituted plant material. Band casting typically employs a slurry of finely divided plant parts mixed with a binder such as gum arabic, guar gum, alginate, xanthan, cellulose and cellulose derivatives (such as carboxy methyl cellulose (CMC), hydroxypropyl methyl cellulose (HPMC)), pectines or starch that is coated onto a steel band and then dried. In one embodiment, the method is performed according to a process similar to the conventional tobacco reconstitution process, which is for example described in U.S. Pat. Nos. 3,353,541; 3,420,241; 3,386,449; 3,760,815; and 4,674,519; which are incorporated herein in their entirety by reference thereto. The method for producing the products of the invention can also be performed by a papermaking process, in order to reconstitute any plant components (such as stems, scraps, leaves, fines, dust and/or shorts) into a paper-like product. Some examples of such processes are described in U.S. Pat. Nos. 3,428,053; 3,415,253; 3,561,451; 3,467,109; 3,483,874; 3,860,012; 3,847,164; 4.182,349; 5,715,844; 5,724,998; and 5,765,570; which are also incorporated herein in their entirety by reference thereto for all purposes. For example, the formation of the products of the invention using papermaking techniques can involve the steps of mixing fruits, herbs, medicinal plants, tea, vegetables and/or spices with water, extracting the soluble ingredients therefrom, concentrating the soluble ingredients, refining the fruits, herbs, medicinal plants, tea, vegetables and/or spices, forming a web, reapplying the concentrated soluble ingredients, drying, and threshing.

In the method of the invention, more specifically with respect to the non-soluble portion (solid plant particles) used in providing the non-impregnated fiber web of the invention, ie. the sheet-like product in step d), the plant is not tobacco, wood pulp, cotton, textiles, jute flax, Indian hemp, hemp, hoopvine, kenaf, nettles, ramie, aback, bamboo fiber, banana (especially banana bark), bowstring hemp, coir (fiber from the coconut shell), esparto, henequen, kapok, milkweed, papaya, phormium ("New Zealand Flax"), sisal, raffia, bagasse, pini, aibika or yucca. However, a mixture of a plant mentioned herin in connection with the present invention with any of the aforementioned plants may be utilized. Further to the foregoing listed materials also others materials can be added to improve product physical characteristics, for example cellulose derivatives such as methylcellulose, carboxymethyl cellulose (CMC), hydroxypropyl methyl cellulose (HPMC), starch and starch derivatives such as oxidatively degraded starch, polysaccharides (and their derivatives) such as pectines, gelatins, guar gum, agar, alginates, carrageenans, or synthetic fibers such as the ones made of vinyl chloride or vinyl acetate, polyethylene, polypropylene, polyesters.

Once extracted, the insoluble, solids portion can optionally be subjected to one or more mechanical refiners to produce a fibrous pulp. Some examples of suitable refiners can include disc refiners, conical refiners, and the like, well known to a skilled person. The pulp from the refiner can then be transferred to a papermaking station (not shown) that includes a forming apparatus, which may include, for example, a forming wire, gravity drain, suction drain, felt press, Yankee dryer, drum dryers, etc. In such a forming apparatus, the pulp is laid onto a wire belt forming a sheet-like shape and excess water is removed by the gravity drain and suction drain and presses. Once separated from the insoluble portion of the plant solution (plant extract), the soluble portion can optionally be concentrated using any known type of concentrator, such as a vacuum evaporator.

In some embodiments of the invention, a wet strength agent may be added to the fibrous portion in order to reduce potential degradation of the reconstituted material when it is brought into contact with a liquid (e.g. water), such as upon infusion in water. Any suitable we strength agent preferably selected for food applications may be used such as polyamide-epichlorohydrin resins, polyamine-epichlorohydrin resins, poly(aminoamide)-epichlorohydrin resins, urea-formaldehyde resins; melamine-formaldehyde resins; alkyl ketene dimer; alkyl succinic anhydride; polyvinylamines; oxidized polysaccharides (such as oxidatively degraded starch); glyoxalated polyacrylamide resins; polyimines such as polyethyleneimine. Wet strength agents are well known to the skilled person and described in Ingredients Standards, such as BFR (Bundesinstitut für Risikobewertung) XXXVI and BFR XXXVI/1 or FDA (Food & Drug Administration) 21 CFR 176.170, FDA 21 CFR 176.110, FDA 21 CFR 176.120, FDA 21 CFR 176.1180. The wet strength agent is for example used in an amount of about 0.1% w/w to about 20% w/w, preferably of about 1% w/w to about 10% w/w, more preferably of about 5% w/w. The wet strength agent is preferably added to the fibrous portion when or before making the sheet-like product (see step d) above).

In one embodiment, the water used for extraction is hot water, preferably of about 30 to 100° C., 40 to 90° C., or 50- to 80° C., or more preferably of about 70° C.

In one embodiment, the coating ratio of solubles portion onto the fiber web is about 5% to 80% (w/w), 10 to 70% (w/w), or more preferably between 20 and 50% (w/w). In some embodiments, the coating ratio or soluble portion that is added back to the base web (fiber web) is similar to the portion of soluble material contained in and extracted from the original plant (so called "standard level").

In one embodiment, the base weight of the final product is about 20 to about 200 $g/m^2$ (dry basis), more preferably about 90 to about 120 $g/m^2$.

The extraction time depends on the fruits, herbs, medicinal plants, tea, vegetables and/or spices subjected to the extraction process. In one embodiment of the invention, the extraction time is about 15 to 60 minutes, preferably 45 minutes.

In one embodiment of the method of the invention, the extracting step is performed using components of a blend of plants, in another embodiment, extracting step is performed using components of a single plant.

Extraction may also be performed by means other than using hot water, namely by extraction with supercritical gases, such as carbon dioxide, or by using, for example, ethanol, hexane, acetone, R134a (1,1,1,2-tetrafluoroethane), carbon dioxide and hydrofluorocarbons. In one embodiment, the extraction can be carried out by using at least one solvent at room temperature and under atmospheric pressure. Extraction may also be performed by using a mixture of different solvents. In another embodiment, extraction may be performed using at least one solvent, such as for example R134a or carbon dioxide, at different temperatures and at different pressures and different states (liquid or gaseous). For example, extraction may be performed using solvents in a liquid state (such as solvent that are volatile or non-volatile at room temperature), in a subcritical state (such as water at a temperature above 100° C. and a pressure above 1 bar), or in a supercritical state (such as carbon dioxide at a temperature above 31° C. and a pressure above 73 bar).

Certain plants may require specific extraction conditions (time, temperature, solid/liquid ratio) due to the ingredients contained therein, which may be temperature sensitive or must not be subjected to certain extraction conditions. For example, extraction of lycopene from tomatoes we must be performed by using specific enzymes to liberate the product from tomatoes cells. In connection with the present invention, processing aids maybe used to improve extraction, such as pH modifiers (such as, for example, NaOH or organic acids), microwaves, pressure, ultrasound, enzymes such as for example proteases, amylases, cellulases, and/or pectinases. Whenever reference is made herein to "extraction", the term includes the aforementioned alternative extraction means. The extraction used in connection with the present invention can be performed in a continuous or discontinuous matter. The extraction conditions are well known to the skilled artisan and described in standard text books, such as Handbook of Separation Techniques for Chemical Engineers, Third Edition (March 1997), Philip A. Schweitzer, McGraw-Hill Inc.

In one embodiment, the extraction and/or pressing may be performed using at least a portion of the plant material, fresh, frozen or dried, or selected from roots, bark, seeds, stems, leaves, flowers and fruit.

Separation of the soluble portion (plant extract) from the non-soluble portion (solid plant particles) can be performed by separating the liquid phase from the solid phase, such as by filtration, with or without pressure, by centrifugation or other methods commonly used in the laboratory and well-known to the skilled person.

In a preferred embodiment of the invention, the plant used in the method of the invention is tea (*Camellia sinensis*), and the extraction is performed for about 45 minutes with water at about 70° C.

In one embodiment of the method where a mixture or blend of plants is used, the non-soluble portion of the plant is mixed with the non-soluble portion of at least one further plant prior to preparing the sheet.

Certain embodiments of the method of the invention use the soluble portion of step b) or concentrated soluble portion of step e), which is mixed with the soluble portion or concentrated soluble portion of at least one further plant prior to applying the soluble portion or concentrated soluble portion to the sheet.

For certain applications it is desirable to adjust the composition by adding or removing ingredients or components to or from the plant extract and/or the non-soluble plant particles prior to producing the final product of the invention. Such adjustment may be performed to modify/improve chemical, physical and/or sensory characteristics of the finished product. The invention thus encompasses methods, further comprising the step of adding or removing ingredients from the soluble portion (plant extract) and/or from the non-soluble portion (solid plant particles) prior to applying the soluble portion of step b) or concentrated soluble portion of step e) to the sheet of step d).

In some embodiments, the sheet or sheet-like product which is obtained in step g) is a web or fiber-web. The sheet-like product or web may be used in different sizes and shapes. In some cases, the composition of step g) is further cut or broken into small regularly or irregularly shaped forms. Alternatively, the composition is brought or formed into any desired shapes, dimensions and formats, such as sheets, leafs (or leaf-like shapes), sticks, bands, cups, mugs, bowls, flasks, kettles, bottles or the like, straws or tubes, discs or sheets and the like, as described below. In addition to cutting or breaking the sheet or fibrous web to a desired size and/or shape or forming the same into to a desired size and/or shape, it may be dried to the desired final moisture content.

In accordance with the present invention the plant is selected from the group consisting of fruits, herbs, medicinal plants, tea, vegetables and spices, including mixtures thereof, such as mixtures of herbs and vegetables. In one embodiment, the fruits, herbs, medicinal plants, tea, vegetables and spices are for example selected from artemisia, balm, basil, chamomile, chive, cloves, coffee, coriander, dill, garlic, ginger, ginseng, gingko, jasmine, lavender, mint, orange blossom, oregano, persil, rooibos, rasa centifolia, rosemary, thyme, turmeric, sage, pepper, chili pepper, Stevia Rebaudiana, tarragon, white tea, yellow tea, green tea, oolong tea, black tea, pu-erh tea, vanilla, red or green vine, violet and/or willow.

In some embodiments of the invention, the plant is for example selected from the group consisting of culinary herbs and spices such as:

Ajwain, carom seeds (*Trachyspermum ammi*), Akudjura (*Solanum centrale*), Alexanders (*Smyrnium olusatrum*), Alkanet (*Alkanna tinctoria*), Alligator pepper, mbongo spice (mbongochobi), hopper pepper (*Aframomum danielli, A. citratum, A. exscapum*), Allspice (*Pimenta dioica*), Angelica (*Angelica archangelica*), Anise (*Pimpinella anisum*), Aniseed myrtle (*Syzygium anisatum*), Annatto (*Bixa orellana*), Apple mint (*Mentha suaveolens*), Asafoetida (*Ferula assafoetida*), Asarabacca (*Asarum europaeum*), Avens (*Geum urbanum*), Avocado leaf (*Peresea americana*), Barberry (*Berberis vulgaris* and other *Berberis* spp.), Basil, sweet (*Ocimum basilicum*), Basil, lemon (*Ocimum×citriodorum*), Basil, Thai (*O. basilicum* var. *thyrsiflora*), Basil, Holy (*Ocimum tenuiflorum*), Bay leaf (*Laurus nobilis*), Bay leaf, Indian, *tejpat, malabathrum*, Boldo (*Peumus boldus*), Borage (*Borago officinalis*), Black cardamom (*Amomum subulatum, Amomum costatum*), Black mustard (*Brassica nigra*), Blue fenugreek, blue melilot (*Trigonella caerulea*), Brown mustard (*Brassica juncea*), Caraway (*Carum carvi*), Cardamom (*Elettaria cardamomum*), Carob (*Ceratonia siliqua*), Catnip (*Nepeta cataria*), Cassia (*Cinnamomum aromaticum*), Cayenne pepper (*Capsicum annuum*), Celery leaf (*Apium graveolens*), Celery seed (*Apium graveolens*), Chervil (*Anthriscus cerefolium*), Chicory (*Cichorium intybus*) Chili pepper (*Capsicum* spp.), Chives (*Allium schoenoprasum*), Cicely, sweet cicely (*Myrrhis odorata*), Cilantro, coriander greens, coriander herb (*Coriandrum sativum*), Cinnamon, Indonesian (*Cinnamomum burmannii, Cassia vera*), Cinnamon, Saigon or Vietnamese (*Cinnamomum loureiroi*), Cinnamon, true or Ceylon (*Cinnamomum verum, C. zeylanicum*), Cinnamon, white (*Canella winterana*), Cinnamon myrtle (*Backhousia myrtifolia*), Clary, Clary sage (*Salvia sclarea*), Clove (*Syzygium aromaticum*), Coriander seed (*Coriandrum sativum*), Costmary (*Tanacetum balsamita*), Cuban oregano (*Plectranthus amboinicus*), Cubeb pepper (*Piper cubeba*), Cudweed (*Gnaphalium* spp.), Culantro, culangot, long coriander (*Eryngium foetidum*), Cumin (*Cuminum cyminum*), Curry leaf (*Murraya koenigii*), Curry plant (*Helichrysum italicum*), Dill seed (*Anethum graveolens*), Dill herb or weed (*Anethum graveolens*), Elderflower (*Sambucus* spp.), Epazote (*Dysphania ambrosioides*), Fennel (*Foeniculum vulgare*), Fenugreek (*Trigonella foenumgraecum*), Filé powder, gumbo filé (*Sassafras albidum*), Fingerroot, *krachai, temu kuntji* (*Boesenbergia rotunda*), Galangal, greater (*Alpinia galanga*), Galangal, lesser (*Alpinia officinarum*), Galingale (*Cyperus* spp.), Garlic chives (*Allium tuberosum*), Garlic (*Allium sativum*), Garlic, elephant (*Allium ampeloprasum* var. *ampeloprasum*), Ginger (*Zingiber officinale*), Ginger, torch, *bunga siantan* (*Etlingera elatior*) (Indonesia), *Golpa*, Persian hogweed (*Heracleum persicum*) (Iran), Grains of paradise (*Aframomum melegueta*), Grains of Selina, Kani pepper (*Xylopia aethiopica*), Horseradish (*Armoracia rusticana*), *Houttuynia cordata* (Vietnam), Huacatay, Mexican marigold, mint marigold (*Tagetes minuta*), Hyssop (*Hyssopus officinalis*), Indonesian bay leaf, *daun salam* (*Syzygium polyanthum*), Jasmine flowers (*Jasminum* spp.), (*Allium hypsistum*) (Nepal), Juniper berry (*Juniperus communis*), Kaffir lime leaves, Makrud lime leaves (*Citrus hystrix*) (Southeast Asia), Kala zeera (or kala jira), black cumin (*Bunium persicum*) (South Asia), Kawakawa seeds (*Macropiper excelsum*) (New Zealand), *Kencur, galangal, kentjur* (*Kaempferia galanga*), *Keluak, kluwak, kepayang* (*Pangium edule*), *Kinh gioi, Vietnamese balm* (*Elsholtzia ciliata*), Kokam seed (*Garcinia indica*) (Indian confectionery), *Korarima*, Ethiopian cardamom, false cardamom (*Aframomum corrorima*) (Eritrea), *Koseret* leaves (*Lippia adoensis*) (Ethiopia), Lavender (*Lavandula* spp.), Lemon balm (*Melissa officinalis*), Lemongrass (*Cymbopogon citratus, C. flexuosus*, and other *Cymbopogon* spp.), Lemon ironbark (*Eucalyptus staigeriana*) (Australia), Lemon myrtle (*Backhousia citriodora*) (Australia), Lemon verbena (*Lippia citriodora*), Leptotes bicolor (Paraguay and southern Brazil), Lesser calamint (*Calamintha nepeta*), *nipitella, nepitella* (Italy), Licorice, liquorice (*Glycyrrhiza glabra*), Lime flower, linden flower (*Tilia* spp.), Lovage (*Levisticum officinale*), Mace (*Myristica fragrans*), *Mahlab*, St. Lucie cherry (*Prunus mahaleb*), Marjoram (*Origanum majorana*), Marsh mallow (*Althaea officinalis*), Mastic (*Pistacia lentiscus*), Mint (*Mentha* spp.) 25 species, hundreds of varieties, Mountain horopito (*Pseudowintera colorata*) 'Pepper-plant' (New Zealand), Musk mallow, abelmosk (*Abelmoschus moschatus*), Mustard, black, mustard plant, mustard seed (*Brassica nigra*), Mustard, brown, mustard plant, mustard seed (*Brassica juncea*), Mustard, white, mustard plant, mustard seed (*Sinapis alba*), Nasturtium (*Tropaeolum majus*), Nigella, kalonji, black caraway, black onion seed (*Nigella sativa*), Njangsa, djansang (*Ricinodendron heudelotii*) (West Africa), Nutmeg (*Myristica fragrans*), Neem, Olida (*Eucalyptus olida*) (Australia), Oregano (*Origanum vulgare, O. heracleoticum*, and other species), Orris root (*Iris germanica, I. florentina, I. pallida*), Pandan flower, kewra (*Pandanus odoratissimus*), Pandan leaf, screwpine (*Pandanus amaryllifolius*, Paprika (*Capsicum annuum*), Paracress (*Spilanthes acmella, Soleracea*) (Brazil), Parsley (*Petroselinum crispum*), Pepper: black, white, and green (*Piper nigrum*), Pepper, Dorrigo (*Tasmannia stipitata*) (Australia), Pepper, long (*Piper longum*), Pepper, mountain, Cornish pepper leaf (*Tasmannia lanceolata*), Peppermint (*Mentha piperata*), Peppermint gum leaf (*Eucalyptus dives*), Perilla, shiso (*Perilla* spp.), Peruvian pepper (*Schinus molle*), *Pandanus amaryllifolius*, Brazilian pepper or Pink pepper (*Schinus terebinthifolius*), Quassia (*Quassia amara*) (bitter spice in aperitifs and some beers and fortified wines), Ramsons, wood garlic (*Allium ursinum*), Rice paddy herb (*Limnophila aromatica*) (Vietnam), Rosemary (*Rosmarinus officinalis*), Rue (*Ruta graveolens*), Safflower (*Carthamus tinctorius*), for yellow color, Saffron (*Crocus sativus*), Sage (*Salvia officinalis*), Saigon cinnamon (*Cinnamomum loureiroi*), Salad burnet (*Sanguisorba minor*), Salep (*Orchis mascula*), Sassafras (*Sassafras albidum*), Savory, summer (*Satureja hortensis*), Savory, winter (*Satureja montana*), Silphium, silphion, laser, laserpicium, lasarpicium (Ancient Roman cuisine, Ancient Greek cuisine), Shiso (*Perilla frutescens*), Sorrel (*Rumex acetosa*), Sorrel, sheep (*Rumex acetosella*), Spearmint (*Mentha spicata*), Spikenard (*Nardostachys grandiflora* or *N. jatamansi*), Star anise (*Illicium verum*), Sumac (*Rhus coriaria*), Sweet woodruff (*Galium odoratum*), Szechuan pepper, Sichuan pepper (*Zanthoxylum piperitum*), Tarragon (*Artemisia dracunculus*), Thyme (*Thymus vulgaris*), Thyme, lemon (*Thymus×citriodorus*), Turmeric (*Curcuma longa*), Vanilla (*Vanilla planifolia*), Vietnamese cinnamon (*Cinnamomum loureiroi*), Vietnamese coriander (*Persicaria odorata*), Voatsiperifery (*Piper borbonense*), Wasabi (*Wasabia japonica*), Water-pepper, smartweed (*Polygonum hydropiper*), Watercress (*Rorippa nasturtium-aquatica*), Wattleseed (from about 120 spp. of Australian *Acacia*), White mustard (*Sinapis alba*), Wild betel (*Piper sarmentosum*) (Southeast Asia), Wild thyme (*Thymus serpyllum*), Willow herb (*Epilobium parviflorum*), Winter savory (*Satureja montana*), Wintergreen (*Gaultheria procumbens*), Wood avens, herb bennet (*Geum urbanum*), Woodruff (*Galium odoratum*), Wormwood, absinthe (*Artemisia absinthium*) Yellow mustard (*Brassica hirta=Sinapis alba*) Yerba buena, any of four different species, many unrelated, Zd'atar (herbs from the genera *Origanum, Calamintha, Thymus*, and/or *Satureja*), Zedoary (*Curcuma zedoaria*).

In some embodiments of the invention, the plant is selected from the group consisting of teas and herbal teas such as:

Anise tea (seeds or leaves), Asiatic penny-wort leaf, Artichoke tea, Bee Balm, Boldo, Burdock, Caraway tea, Catnip tea, Chamomile tea, Che Dang tea (*Ilex causue* leaves), Chinese knot-weed tea, Chrysanthemum tea, Cinnamon, Coca tea, Coffee tea leaves and coffee cherry tea, Cerasse, Citrus peel (including bergamot, lemon and orange peel), Dandelion coffee, Dill tea, Echinacea tea, Elderberry, European Mistletoe (*Viscum album*), Essiac tea, Fennel, Gentian, Ginger root, Ginseng, Goji, Hawthorn, Hibiscus, Ho Yan Hor Herbal Tea, Honeybush, Horehound, Houttuynia, Hydrangea tea (*Hydrangea serrata* Amacha), Jiaogulan, Kapor tea, Kava rout, Kratom, Kuzuyu, Labrador tea, Lapacho (also known as *Taheebo*), Lemon Balm, Lemon and ginger tea, Lemon grass, Luo han guo, Licorice root, Lime blossom, Mint, Mountain Tea, Neem leaf, Nettle leaf, New Jersey Tea, Noni tea, Oksusu cha, Pennyroyal leaf, Pine tea, Qishr, Red clover tea, Red raspberry leaf, Roasted barley tea, Roasted wheat, Rooibos (Red Bush), Rose hip, Roselle petals (species of Hibiscus; aka Bissap, Dab, etc.), Rosemary, Sagebrush, California Sagebrush, Sage, Sakurayu, Salvia, Scorched rice, Skullcap, Serendib (tea), Sobacha, Spicebush (Lindera benzoin), Spruce tea, Staghorn sumac fruit, Stevia, St. Johns Wort, Tea (*Camellia sinensis*), Thyme, Tulsi, Holy Basil, *Uncaria tomentosa*, commonly known as Cat's Claw, Valerian, Verbena (Vervains), Vetiver, Wax gourd, Wong Lo Kat, Woodruff, and/or Yarrow.

In some embodiments of the invention, the plant is for example selected from the group consisting of medicinal plants such as:

Açai (*Euterpe oleracea*, Alfalfa (*Medicago sativa*), Arnica (*Arnica Montana*, Asthma weed (*Euphorbia hirta*), Astragalus (*Astragalus propinquus*), Barberry (*Berberis vulgaris*), Belladonna (*Atropa belladonna*), Bilberry (*Vaccinium myrtillus*), Bitter gourd (*Momordica charantia*), Bitter leaf (*Vernonia amygdalina*), Bitter orange (*Citrus×aurantium*), Black cohosh (*Actaea racemosa*), Blessed thistle (*Cnicus benedictus*), Blueberries (genus *Vaccinium*), Burdock (*Arctium lappa*), Cat's claw (*Uncaria tomentosa*), Cayenne (*Capsicum annuum*), Celery (*Apium graveolens*), Chamomille (*Matricaria recutita* and *Antemis nobilis*), Chaparral (*Larrea tridentata*), Chasteberry (*Vitex agnus-castus*), Chili (*Capsicum frutescens*), Cinchona, Clove (*Syzygium aromaticum*), Coffee senna (*Cassia occidentalis*), Comfrey (*Symphytum officinale*), Cranberry (*Vaccinium macrocarpon*), Dandelion (*Taraxacum officinal*), Dong quai (*Angelica sinensis*), Elderberry (*Sambucus nigra*), Eucalyptus (*Eucalyptus globulus*) European Mistletoe (*Viscum album*), Evening primrose (*Oenothera* spp.), Fenugreek (*Trigonella foenum-graecum*), Feverfew (*Tanacetum parthenium*), Flaxseed (*Linum usitatissimum*), Garlic (*Allium sativum*), Ginger (*Zingiber officinale*), Gingko (*Gingko biloba*), Ginseng (*Panax ginseng* and *Panax quinquefolius*), Goldenseal (*Hydrastis canadensis*), Grape (*Vitis vinifera*), Guava (*Psidium guajava*), Hawthorn (specifically *Crataegus monogyna* and *Crataegus laevigata*), Hoodia (*Hoodia gordonii*), Horse chestnut (*Aesculus hippocastanum*) Horsetail (*Equisetum arvense*), Jamaica dogwood (*Piscidia erythrina* or *Piscidia piscipula*), Kava (*Piper methysticum*), Kha, Konjac (*Amorphophallus konjac*), Kratom (*Mitagyna speciosa*), Karma (*Sceletium tortuosum*), Lavender (*Lavandula angustifolia*), Lemon (*Citrus limon*), Licorice root (*Glycyrrhiza glabra*), Marigold (*Calendula officinalis*), Marsh mallow (*Althaea officinalis*), Milk thistle (*Silybum marianum*), Neem (*Azadirachta indica*), Noni (*Morinda citrifolia*), Oregano (*Origanum vulgare*), Papaya (*Carica papaya*), Peppermint (*Mentha×piperita*) Purple coneflower (*Echinacea purpurea*), Passion Flower (*Passiflora*), Red clover (*Trifolium pratense*), Rosemary (*Rosmarinus officinalis*), Sage (*Salvia officinalis*), Syrian Rue (aka Harmal) (*Peganum harmala*), St. John's wort (*Hypericum perforatum*), Saw palmetto (*Serenoa repens*), Thunder God Vine (*Triplerygium wilfordii*), Thyme (*Thymus vulgaris*), Tulasi (*Ocimum tenuiflorum* or Holy Basil), Turmeric, (*Curcuma longa*), Umckaloabo (*Pelargonium sidoides*), Valerian (*Valeriana officinalis*), White willow (*Salix alba*), and/or Yerba santa (*Eriodictyon crassifolium*).

As disclosed herin, mixtures of the above-mentioned culinary, herbal and/or medicinal plants are also included as part of the invention.

In a preferred embodiment of the invention, the plant is tea (*Camellia sinensis*), including white tea, yellow tea, green tea, oolong tea, black tea, and/or pu-erh tea, and the like, including mixtures or blends thereof.

In a further embodiment, the invention relates to a fiber-web comprising from about 5% to about 100% (w/w)), preferably at least 10%, at least 20%, at least 30%, at least 40%, at least 50%, at least 60%, at least 70%, at least 80%, at least 90%, or 100%, fibers of fruits, herbs, medicinal plants, tea, vegetables and/or spices. In one embodiment, the fiber-web further comprises cellulosic and/or synthetic fibers, and fibers of fruits, herbs, medicinal plants, tea, vegetables and/or spices in a ratio of for example: 40/60 (w/w), 60/40 (w/w) or 20/80 (w/w). In another embodiment of the invention, the fiber-web of the present invention is obtainable by the method disclosed herein, namely as an intermediate product in step d) of the said method.

The invention further relates to a composition for making a beverage (drink, tea etc), obtainable by the method of the present invention disclosed herein.

The invention also includes the use of the composition of the invention for making a beverage (drink, tea etc.), or broth, or for culinary use or use in cooking, respectively. i.e. as a herb and spice mixture such as a bouquet garni instead of a conventional bouquet garni, as described in this description. Specifically, the invention includes the use of the composition of the invention for as a drink (beverage), as a food or food product, for culinary or cooking purposes, or for medicinal or aromatic applications and the like, as described above and in the following description and examples.

Also included is a beverage obtainable by contacting water with the composition of the invention.

In one embodiment of the invention, the fiber-web comprises from about 5% to about 100% (w/w)), preferably at least 10%, at least 20%, at least 30%, at least 40%, at least. 50%, at least 60%, at least 70%, at least 80%, at least 90%, or 100%, fibers of fruits, herbs, medicinal plants, tea, vegetables and/or spices. For certain applications, the fiber-web may further comprise cellulosic and/or synthetic fibers. In a particular embodiment, the fiber-web comprises fibers of (i) fruits, herbs, medicinal plants, and/or tea, vegetables and/or spices and (ii) cellulosic fibers and/or synthetic fibers in a ratio of 40/60 (w/w), 60/40 (w/w) or 80/20 (w/w).

The invention further relates to a fiber-web, obtainable by the method of the invention, namely in step d).

In some embodiments of the invention, the fiber-web further comprises a coating or impregnation with soluble portion (plant extract) of fruits, herbs, medicinal plants, or tea. The coating or impregnation is obtained by various methods known to the skilled person, such as applying to or treating the fiber-web or sheet-like structure with a plant extract, such as in a bath or by special application means, such as sprayers. In addition, various other ingredients, such as flavor or color treatments, can also be applied to the web. If applied with the soluble portion and/or other ingredients, the fibrous sheet material can, in some embodiments, then be dried using, for example, a tunnel dryer, to provide a sheet having a typical moisture content of less than 20% by weight, and particularly from about 9% to about 14% by weight.

The invention thus also relates to an impregnated or coated fiber-web, obtainable by the method of the invention, namely in step g).

According to a further embodiment, the fiber-web of the invention further comprises a coating or an impregnation with the soluble portion (plant extract) of said fruits, herbs, medicinal plants, or tea. In another embodiment of the invention, the fiber-web of the present invention is obtainable by the method disclosed herein, namely as the end product in step g) of said method.

In a further embodiment, the invention relates to a tea product or container, which is a tea bag comprising the fiber-web referred to herein, which is either impregnated with the soluble portion (plant extract) of said fruits, herbs, medicinal plants, or tea, or which is not impregnated. The tea bag may be empty or filled, ie, the tea bag may further comprise inside a sample or portion of fruits, herbs, medicinal plants, or tea, such as in the form of tea leaves, tea dust or the like. Even though the tea bag may be produced industrially on conventional tea bagging machines, in this embodiment, the product is made from entirely natural products, most preferably the same plant or herb as the one used for making the beverage, wherein the product avoids using conventional cellulose-based tea bags.

In one embodiment, the tea bag may be impregnated with tea extract, wherein said product provides an increased tea aroma when making the infusion, in particular when the tea bag is filled with, for example, tea leafs or tea dust. In a preferred embodiment, the tea bag comprising the fiber-web referred to herein, is impregnated with the soluble portion of a certain kind of tea (tea extract) and also filled with the same kind of tea, for example in the form of tea leafs or tea dust. Alternatively, the impregnation can be made using a different plant or herb as used for the filling of the bag, such as, for example, the rind of the bergamot orange, a fragrant citrus fruit typically used to provide the distinctive flavour and aroma of Earl Grey tea. In this case, Earl Grey tea products can be prepared from unflavoured tea leaves, simply by adding the flavour and aroma of the bergamotte orange in the form of the tea bag coating. This procedure facilitates the production process, as the tea company is not required to aromatize different batches of tea but can simply use non-aromatized tea instead, the latter of which is packaged into tea bags specifically aromatized using different impregnations. In another embodiment applying this principle, a mixture of teas and/or other plants can be utilized for making tea bags, where tea is placed into the tea bag, wherein the tea bag is made, for example, of mint leaves.

Alternatively, the tea product or container of the invention is provided in the form of a tea pod, tea pad or tea capsule instead of a tea bag, such as for either direct immersion or to be used in connection with conventional tea machines or coffee brewing machines (such as Nestlé Special.T®, or Nespresso®).

The products of the invention enable a more efficient infusion (100% solubles are extracted from the plant) in the sense that more solubles can be released than natural plant ingredients for a given weight of material. The products also provide a faster infusion (than with a conventional infusion made from the vegetal material in its natural non converted form). Specifically, the compositions of the invention have improved efficiency in boiling water or in non-heated water or water at room temperature.

The process for making the compositions of the invention also allows for specifically adjusting the final composition of the products, such as to remove from the soluble or the non-soluble portion(s) for example foreign matters, components altering taste and/or odor, or caffeine, nicotine, pesticides, aluminum, heavy metals, mycotoxins, toxicants and allergenic molecules such as coumarin, farnesol, geraniol, limonene, linalol, safrole, methyleugenol, or by adding to the soluble or the non-soluble portion(s) for example desirable additives, such as sweeteners, sugars, flavors, casings, vitamins, colorants, minerals, taste enhancers.

In another embodiment, the soluble portion in the reconstituted material of the invention can be precisely adjusted (decreased as compared to standard level, at standard level, or increased as compared to standard level). A key benefit is that the level of ingredients in the reconstituted material can be precisely increased to a level higher than in the original natural form, thus allowing for more concentrated (more intense) drinks, teas or broths. The adjustment of ingredients can also guarantee a consistent, standardized level of delivered ingredients to compensate natural variations of active ingredients in plants.

Preferably, the method of the invention also allows for reduction of undesired compounds from the material, such as to selectively remove undesired components (such as, for example but not limited to, natural ingredients, caffeine, nicotine, aluminum, heavy metals, pesticides, impurities or the like). For example, it is possible to remove components from either the soluble portion (plant extract) or from the non-soluble portion (solid plant particles) or both by liquid-liquid extraction, physical adsorption, centrifugation, chromatography, crystallization, decantation, by use of a demister, drying, distillation, electrophoresis, elutriation, evaporation, solid phase or liquid-liquid extraction, flotation, flocculation, filtration (for example using membranes), vapor-liquid separation, and/or sublimation and other means well known to the skilled person, preferably before applying the plant extract to the base web.

In connection with adding ingredients, extracts of different sources and origins, flavors, coloring agents or the like may be used, such as clorophyll, anthocyans, caramel, caroteinoids. For example, when using tea or herbs it is possible to include L-menthol at various quantities (such as 6% or 15%) in the finished product. Products so obtained have a distinctive taste and aroma of menthol. In one embodiment, eugenol, thymol or plant extracts/concentrates can be added to the reconstituted bouquet garni of the invention.

The present invention also allows to blend various plants and herbs. In one example, instead of using single plants, such as tea or mint leaves, tea may be replaced by a mixture of, for example, 50% tea and 50% mint leaves (w/w); 50% verbena and 50% mint (w/w); 30% cinnamon and 30% tea and 10% licorice and 10% chamomile and 10% red vine and 10% roobois (w/w); and many other combinations.

The combination of different plant materials through the reconstitution process into a single fiber web impregnated with extracts from different plants (the same plant or blends) offers new taste experiences and additive or synergistic effects. For example, it is known that combinations of certain plant extracts or combinations of certain plant ingredients have additive or synergistic effects, such as, for example, a mixture of hops and valerian extracts for use in treating insomnia and vigilance (Blumenthal and al., J. Herbal Medicine, expanded Commission E monographs, American Botanical Council, Austin, 2000, 394-400), or mixtures of oregano and cranberry extracts for use in treating *H. pylori* infections (Lin et al., Appl. Environ. Microbiol. December 2005, vol. 71, no. 12, 8558-8564), or different mixtures of extracts of *S. baicalensis, D. morifolium, G. uralensis* and *R. rubescens* tested for their additive or synergistic effect in prostate cancer cell lines (Adams et al., Evid. Based Complement Alternat Med, 2006 March; 3(1); 117-124).

In the context of the present invention, the reconstituted plant material or product of the invention may be used to blend a single plant (or a mixture of different plants) together with natural materials, such as, for example, reconstituted black tea with natural tea material or reconstituted mint (*Mentha* spp.) with natural green tea material, in order to improve the quality (such as the chemical constitution, the consistency or sensory profile and characteristics) of the product or blend.

It has been found that some beverages are particularly less astringent and bitter when prepared from the reconstituted plant material or product of the invention as compared to original material from which the reconstituted plant material or product of the invention was prepared. This is, for example, the case for green tea, which is less astringent and bitter when made from a reconstituted green tea product according to the invention as compared to a conventional infusion of green tea.

The production method also provides for reducing microbiological load of the final products because of the high temperatures during the papermaking process.

The products of the invention provide a light material having a small surface, which allows economic packaging/shipping. For the consumer, the products of the invention are easy to transport and easy to use. Specifically, it has been found that the products of the invention are easily infusible in even cold water. This has particular advantages for consumers in cases where no heating or electricity is available for preparing hot water.

The products are further available in all shapes, dimensions and formats, such as sheets, leafs (or leaflike shapes), sticks, bands, cups, mugs, bowls, flasks, kettles, bottles or the like, straws or tubes, discs or sheets and the like, and can be customized with a logo. These products are convenient for the customer to be put or dipped into hot or cold water to produce the beverage of interest. Alternatively, hot or cold water is poured into or injected into said cups, mugs, bowls, flasks, kettles, bottles or the like, to produce the beverage of interest. In the case of staws or tubes impregnated with the desired plant extract on the inner side of the stave or tube, infusion occurs when sucking cold or hot liquid (e.g. water) through the straw or tube. Alternatively, the straw or tube is simply placed in cold or hot water, such as for example in a kettle or glass, to produce the beverage or broth of interest. In the case of cups, mugs, bowls, flasks, kettles, bottles or the like, preferably (only) the inner side of the cups, mugs, bowls, flasks, kettles, bottles or the like are impregnated with the plant extract of interest. By pouring cold or hot liquid (such as water) into the cups, mugs, bowls, flasks, kettles, bottles or the like, immersion and infusion take place to provide the beverage or broth of interest. In one embodiment of the invention, the cups, mugs, bowls, flasks, kettles, bottles or the like are entirely made of the products of the invention, i.e. made of the composition of the invention comprising a layer of fibrous plant product and a plant extract applied thereto. In this case, the cups, mugs, bowls, flasks, kettles, bottles or the like are preferably disposable. Thus, the customer would simply need cold or hot liquid, such as cold or hot water, to make the infusion, beverage or broth of interest. In an alternative embodiment, the products of the invention, i.e. the compositions of the invention comprising a layer of fibrous plant product and a plant extract applied thereto, form the inner coating or lining of cups, mugs, bowls, flasks, kettles, bottles or the like. These products may be provided either as disposable, such as (bio-)degradable, or as non-disposable products, depending on the material used for producing the cups, mugs, bowls, flasks, kettles, bottles or the like. Also, the inner coating or lining of cups, mugs, bowls, flasks, kettles, bottles or the like may either be in the form of a permanent coating or lining, i.e. fixed to the inner walls of said cups, mugs, bowls, flasks, kettles, bottles or the like, or it may be in the form of a replaceable product (like a cartridge) having the same shape as the cup, mug, bowl, flask, kettle, bottle or the like, in order to be disposed of after use (i.e. after preparing the infusion, beverage or broth) and replaced by a new product in order to prepare a new infusion, beverage or broth.

In one embodiment of the invention, the products are provided in the form of kits comprising said sheets, leafs (or leaf-like shapes), sticks, bands, cups, mugs, bowls, flasks, kettles, bottles or the like, straws or tubes, discs or sheets and the like. In one embodiment, the kits may also comprise extracts of plants of interest, suitable for the customer to impregnate said products before making the desired beverage or broth (i.e., first-time impregnation), or to re-impregnate said products after use to make further beverages or broths (i.e., reusable version of a product that was already pre-impregnated before its first use). In one embodiment of said kits, the kits comprise various types of plants of interest, i.e. various different fruits, herbs, medicinal plants, tea, vegetables and/or spices, in order to enable the customer to make his/her own blends as desired. In this way, the customer is able to create his/her flavor or taste. In these kits, the different types of plants may be in the form of different sheets, leafs (or leaf-like shapes), sticks, bands, cups, mugs, bowls, flasks, kettles, bottles or the like, straws or tubes, discs or sheets and the like, separately pre-impregnated with said different fruits, herbs, medicinal plants, tea, vegetables and/or spices. Alternatively, the different fruits, herbs, medicinal plants, tea, vegetables and/or spices may be provided in the kits in the form of separate plant extracts (or pre-mixed combinations), in order to be used for re-impregnation as described above.

In one embodiment, where the products of the invention are provided in the form of sheets like sheets of paper, impregnated with the plant extracts of interest as described above, the sheets may form separate pages and be put together like pages of a book. For example one or more page of said book may be impregnated with one type of plant (fruit, herb, medicinal plant, tea, vegetable and/or spice), whereas other pages are impregnated with different types of plants (fruit, herb, medicinal plant, tea, vegetable and/or spice). The pages that are impregnated with a certain plant extract, wherein the extract comprises the extract of either a single plant or a blend of plants, may contain a description of said plant(s) used for the impregnation of said page. The description may be written on or printed to said page using food inks or food dyes. In a preferred embodiment of the "hook" described above, the book is a "tea book", where the impregnations on the individual pages are extracts of different types of tea, wherein separate pages correspond to separate types of tea or blends of tea containing said description of the original tea product used for making the sheets and/or the impregnations. The sheets or pages of the book are suitable for the customer to be used for preparing infusions, beverages or broths. In one embodiment, the pages of the book may be perforated for easy detaching the pages from the book.

Referring to FIGS. 19A thru 19K, various embodiments of products made in accordance with the present disclosure are illustrated. For instance, referring to FIG. 19A, an infusion product dispenser 10 is shown. The infusion product dispenser 10 includes a dispenser housing 12 containing an infusion product 14. The infusion product 14 is contained within the dispenser housing 12 and dispensed through an opening or slot 16. The infusion product 14 comprises a layer of fibrous plant product in which a plant extract has been applied thereto. In the embodiment illustrated in FIG. 19A, the infusion product 14 is in the form of a strip or strips. For instance, in one embodiment, the infusion product 14 may comprise a single strip that is spirally wound within the dispenser housing 12. In this embodiment, a user can pull from the dispenser housing 12 a desired amount of the infusion product 14 for producing a tea or beverage. In one embodiment, the infusion product 14 can be torn or ripped when a desired amount has been withdrawn from the dispenser housing 12. Optionally, the dispenser housing 12 may include a cutting device for cutting the infusion product 14 as the product is being dispensed. For example, in one embodiment, the cutting device may comprise a serrated edge located within or adjacent to the opening or slot 16.

In an alternative embodiment, the infusion product 14 may include perforation lines at periodic intervals. In this embodiment, when removing the infusion product 14 from the dispenser housing 12, a desired portion of the infusion product can be easily detached from the remainder of the strip by tearing along one of the perforation lines.

In still another embodiment, the infusion product 14 may be precut into strips having a desired length. The individual strips can then be held within the dispenser housing 12 in any suitable arrangement. For instance, the strips can be stacked within the dispenser housing or can be spirally wound together. When cut into individual strips, the strips can be arranged within the dispenser housing such that when one strip is removed from the dispenser housing 12, an adjacent strip automatically partially protrudes from the dispenser housing through the opening or slot so that the next strip is accessible for use. In this regard, the individual strips of the infusion product 14 can be interconnected together using, for instance, an adhesive material and/or through a folding arrangement.

Figure 19A:
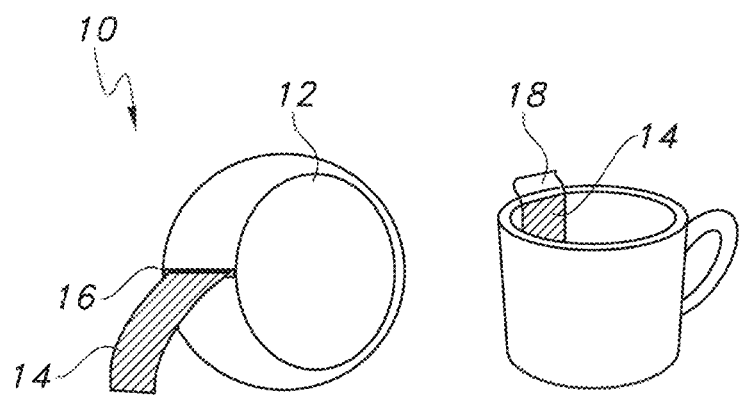
FIG. 19A-K shows reconstituted material in different physical shapes that provide for different kinds of applications.

In one particular embodiment, the infusion product 14 can be contained within the dispenser housing 12 in the form of individual strips. As shown in FIG. 19A, each strip can include a tab portion 18 located at one end of each individual strip. The tab portion 18 can be used for holding and manipulating the infusion product 14 without touching the reconstituted material. The tab portion 18 can be formed in various ways. For instance, in one embodiment, the tab portion 18 may comprise a coating that has been applied to the strip of reconstituted material. The coating can be made, for instance, from a polymer, such as a film forming polymer. Alternatively, the tab portion 18 can be formed by laminating a sheet or film to the strip of reconstituted material. In this embodiment, the layer or sheet laminated to the reconstituted material may comprise a paper, a polymer film, or the like. In still another embodiment, the tab portion 18 can be made from a different material than the reconstituted material and then attached to the strip of the reconstituted material. In this embodiment, the tab portion 18 can be attached to the reconstituted material using any suitable adhesive. The tab portion 18 can be formed from a film, a paper, a nonwoven web, a woven web, a knitted web, or the like.

In one particular embodiment, the tab portion 18 can comprise an adhesive portion for not only manipulating the infusion product 14 but also for adhering the infusion product 14 to an adjacent surface. An adhesive portion can be formed by applying an adhesive material to the strip of reconstituted material or to a different material that is attached to the strip of reconstituted material. The adhesive portion 18 comprises an adhesive material that is completely non-toxic and safe for contact with food products.

As shown in FIG. 19A, the tab or adhesive portion 18 is located at one end of the strip of infusion product 14. In one embodiment, the tab or adhesive portion 18 forms an end tab at the end of the infusion product 14. The tab or adhesive portion 18 generally has a length that is less than 50%, such as less than 40%, such as less than 30%, such as less than 20%, such as less than 15%, such as less than 10% of the total length of the strip. The tab or adhesive portion 18 is generally greater than about 2%, such as greater than about 5% of the entire length of the strip.

The adhesive portion 18 can have various different functions when present in conjunction with the infusion product 14. For instance, as shown in FIG. 19A, the adhesive portion 18 can be used to adhere the infusion strip product 14 to a coffee cup or mug so that the infusion product remains in a certain position while the cup or mug is filled with a liquid, such as cold or hot water. Once a beverage is made from the infusion product, the infusion product can be easily removed from the cup or mug by grasping onto the adhesive portion 18. In this manner, the infusion strip product 14 can be easily attached during use and easily detached after use during the production of a beverage.

In addition to attaching the infusion strip product to an adjacent surface, the adhesive portion 18 can also be used to facilitate the manner in which the strip product is dispensed from the dispenser housing 12. The adhesive portion 18, for instance, can allow each of the individual strips to be temporarily attached together within the dispenser housing 12 within a stack. By interconnecting the individual strips, when one strip is removed from the dispenser housing, an adjacent strip can be pulled through and immerge from the opening 16. In this manner, the individual strips can be easily dispensed from the dispenser housing one at a time.

The adhesive portion 18 can be formed in different ways. In one embodiment, the adhesive portion 18 can be formed by simply applying the adhesive material to a portion of the infusion product strip. Alternatively, the adhesive portion 18 may comprise a substrate treated with the adhesive material and then attached to the infusion strip product. In one embodiment, the adhesive portion 18 may further include a release liner. The release liner may be used to cover the adhesive material prior to use. In this embodiment, when the infusion strip product is to be adhered to an adjacent surface, the release liner can be peeled away and removed from the adhesive portion thereby exposing the adhesive material.

Figure 19B:
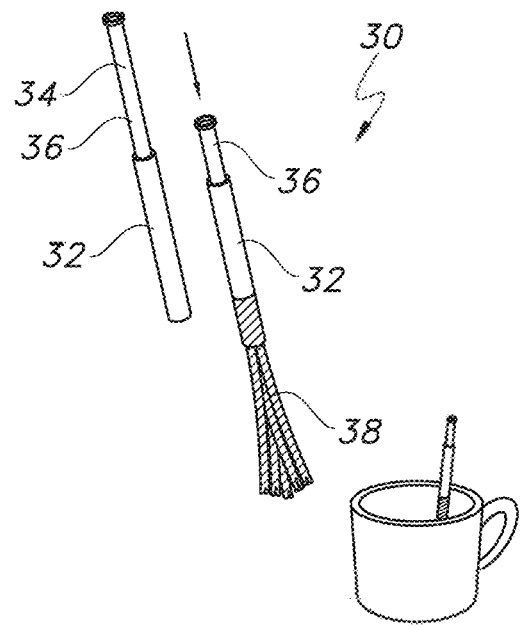
Figure 19C:
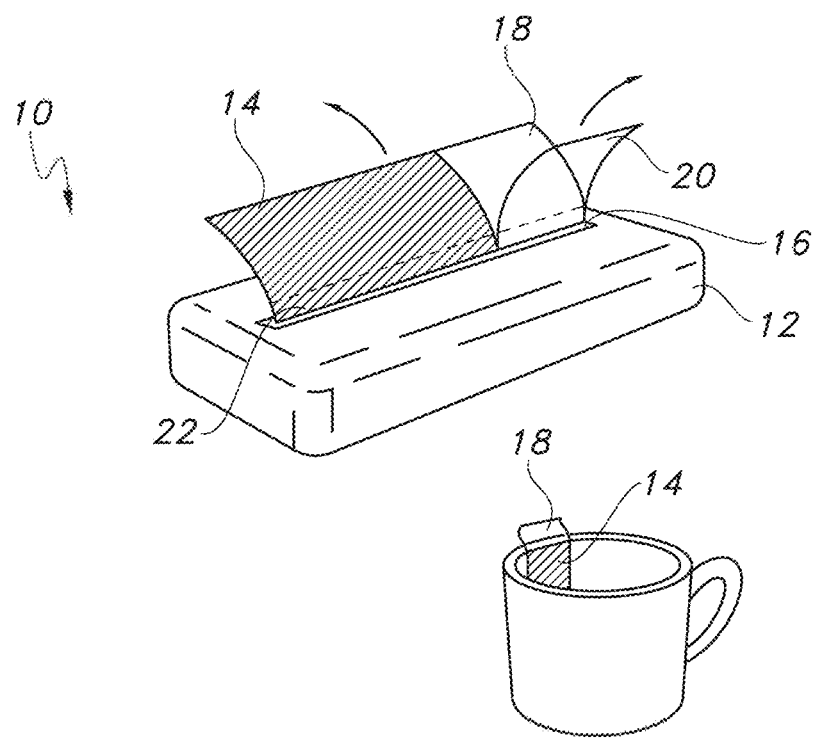

Referring to FIG. 19C, another embodiment of an infusion product dispenser 10 is shown. The dispenser housing 10 includes a dispenser housing 12 that dispenses an infusion product 14. In the embodiment illustrated in FIG. 19G, the dispenser housing 12 has a rectangular shape in comparison to the dispenser housing illustrated in FIG. 19A which has more of a cylindrical shape. In the embodiment illustrated in FIG. 19A, the infusion strip product is dispensed from the dispenser housing in a length-wise direction. In the embodiment illustrated in FIG. 19G, on the other hand, the infusion strip product 14 is dispensed from the dispenser housing 12 in the width direction.

Otherwise, the embodiment illustrated in FIG. 19C can be constructed similar to the embodiment illustrated and described above with respect to FIG. 19A. In the embodiment illustrated in FIG. 19C, for instance, the infusion product 14 can comprise a single strip of product contained within the dispenser housing 12 or can comprise individual strips stacked within the dispenser housing. When a single strip is contained within the dispenser housing 12, the strip can be periodically perforated to allow a user to remove from the strip an individual strip product. Alternatively, the dispenser housing 12 can include an opening or slot 16 that is positioned adjacent to a cutting device, such as a serrated edge 22. The serrated edge 22 can be used to cut the infusion strip product into individual strips having any desired width.

As shown in FIG. 19C, the infusion product 14 includes an adhesive portion 18 for adhering the strip product to an adjacent surface, such as a cup or mug. In the embodiment illustrated in FIG. 19C, the adhesive portion 18 includes a release liner 20 that covers and protects the adhesive material prior to use. The release liner 20 can be made, for instance, from a film, such as a polymer film. In one embodiment, for instance, the release liner 20 can comprise a polyester film. Once an individual strip is removed from the dispenser housing 12, the release liner 20 can be peeled away from the adhesive portion 18 for adhering the strip product to an adjacent surface.

Figure 19D:
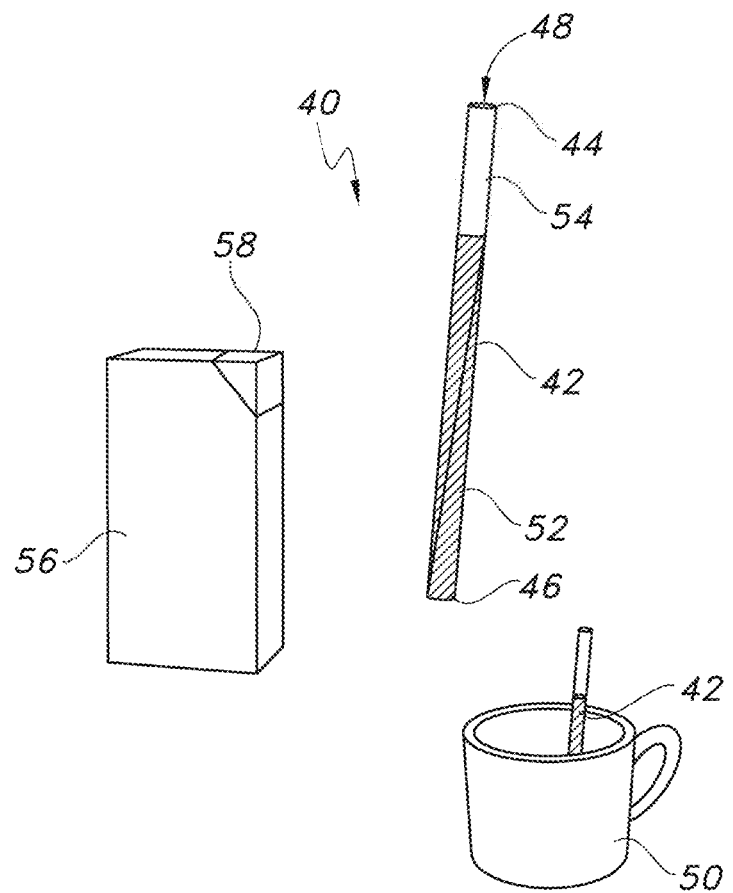
Figure 19E:
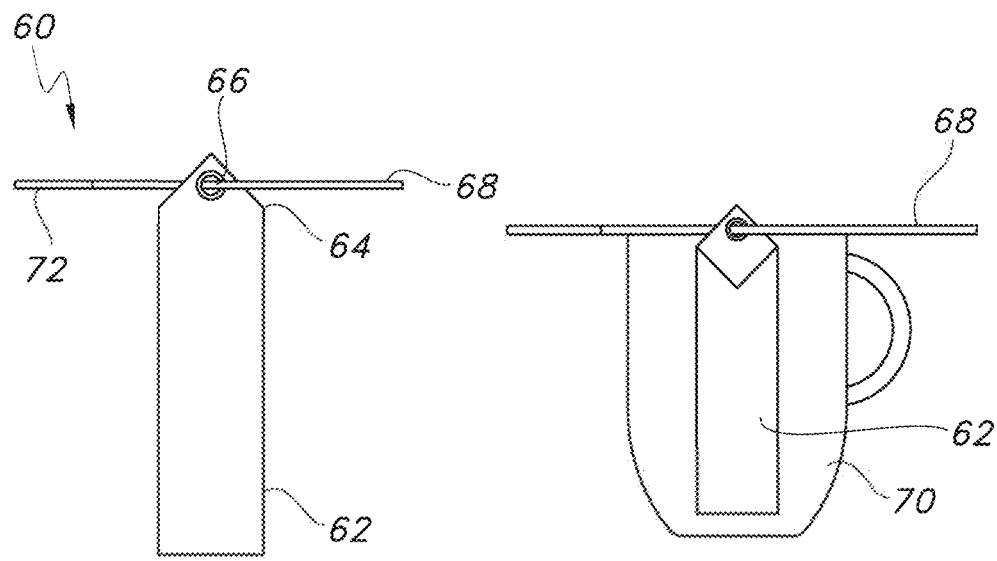
Figure 19F:
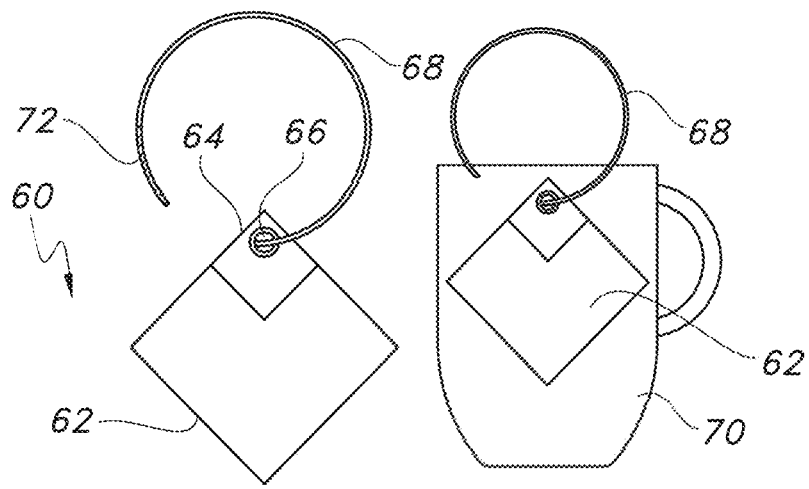
Figure 19G:
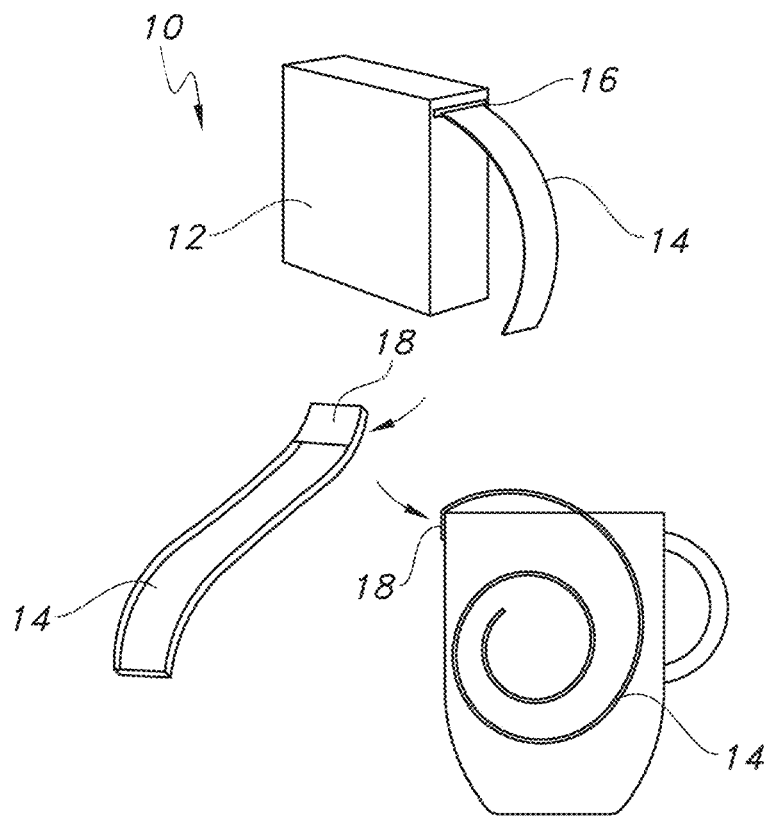

Referring to FIG. 19G, another embodiment of an infusion product dispenser 10 similar to the embodiments illustrated in FIGS. 19A and 19C is shown. Like reference numerals have been used to show the same or similar elements. As shown in FIG. 19G, the infusion product dispenser 10 includes a dispenser housing 12 containing an infusion product 14 in the form of a strip or multiple strips. The dispenser housing 12 includes an opening or slot 16 through which the infusion product 14 is dispensed. The infusion product 14 can comprise a continuous or endless strip within the housing or can comprise individual strips that are stacked or otherwise interconnected within the housing. Each individual infusion strip product 14 can include an adhesive portion 18 for adhering the infusion product to an adjacent surface, such as a cup or mug.

In the embodiment illustrated in FIG. 19G, the infusion product is contained within the dispenser housing within a spirally wound arrangement either as a single strip or as multiple strips. In this manner, each individual strip is dispensed from the dispenser housing in a curved configuration, such as a spiral configuration. As shown in FIG. 19G, for instance, the spiral configuration is maintained when the infusion product is placed in use. By having a spiral configuration or curved configuration, the infusion strip product 14 conveniently fits within the cup or mug even when the strip has a length that is greater than the depth of the mug. For example, the embodiment illustrated in FIG. 19G is particularly well suited for embodiments where the strip 14 has a length of greater than about 2.5 inches, such as greater than about 3 inches, such as greater than about 3.5 inches, such as greater than about 4 inches, such as greater than about 4.5 inches, such as greater than about 5 inches, such as greater than about 5.5 inches, such as greater than about 6.5 inches. The strip generally has a length less than 20 inches, such as less than 12 inches.

The infusion product 14 as shown in FIGS. 19A, 19C, and 19G can be made from a layer of fibrous plant product in which a plant extract has been applied thereto as described above. In one embodiment, the layer of fibrous plant product contains at least one type of tea leaf alone or in combination with various other plant products. The strip or layer can have a basis weight of generally greater than about 20 gsm, such as greater than about 40 gsm, such as greater than about 50 gsm, such as greater than about 60 gsm, such as greater than about 70 gsm, such as greater than about 80 gsm, such as greater than about 90 gsm, such as even greater than about 100 gsm. The layer of fibrous plant product generally has a basis weight of less than about 200 gsm, such as less than about 180 gsm, such as less than about 160 gsm, such as less than about 150 gsm, such as less than about 140 gsm, such as less than about 130 gsm, such as less than about 120 gsm, such as less than about 110 gsm.

Referring to FIG. 19B, another embodiment of an infusion product 30 is shown. In this embodiment, the infusion product 30 includes a sliding member 32 that slides over an infusion product member 34. The infusion product member 34, in the embodiment illustrated in FIG. 19B, includes a shaft member 36 connected to or integral with a plurality of infusion filaments 38. As shown, the sliding member 32 can have a cylindrical configuration and can serve as a protective covering or sheath for the infusion filaments 38 prior to use. During use, the sliding member 32 can be slid over the shaft member 36 for exposing the infusion filaments 38. By exposing the infusion filaments 38, the infusion filaments can be available for producing a beverage, such as by being placed in a cup or mug and contacted with a liquid, such as water.

In one embodiment, the shaft member 36 and the infusion filaments 38 can all be made from a reconstituted material in accordance with the present disclosure. For instance, the reconstituted material can be in the form of a rod in which one end has been fibrillated to form the infusion filaments 38.

In an alternative embodiment, the shaft member 36 can be made from a different material and attached to the infusion filaments 38. For instance, the shaft member 36 can be made from a polymer or plastic material or can be made from a paper or paperboard material.

The infusion filaments 38 comprise the reconstituted material made in accordance with the present disclosure. The infusion filaments 38 can have any suitable shape or form. For instance, the infusion filaments 38 can be in the form of strips, ribbons, or the like. Alternatively, the infusion filaments can have a cross-sectional shape that is curved, such as round or in the shape of an oval. In still another embodiment, the infusion filaments can have a cross-sectional shape that is irregular.

Of particular advantage, the infusion product 30 not only protects the infusion filaments 38 prior to use, but can also conveniently be used as a stirring device when contacting the infusion filaments with a liquid. For instance, as shown in FIG. 19B, the infusion product 30 can serve as a stirring device when placed in a cup or mug and filled with a liquid, such as water.

Referring to FIG. 19D, another embodiment of an infusion product 40 made in accordance with the present disclosure is shown. In the embodiment illustrated in FIG. 19D, the infusion product 40 comprises a cylindrical member 42 made from the reconstituted material of the present disclosure. In one embodiment, the cylindrical member 42 can be made only from the reconstituted material and may comprise a solid rod or stick. In an alternative embodiment, the cylindrical member 42 may comprise a straw or tube. For instance, the straw or tube can include a top 44, a bottom 46, and a hollow passageway 48 that extends from the top to the bottom.

The cylindrical member 42 is well suited for producing a beverage or broth. For instance, as shown in FIG. 19D, the cylindrical member 42 can be placed in a cup or mug 50. A liquid, such as hot or cold water, can be placed in the mug or cup 50 for producing the beverage or broth. The cylindrical member 42 can be used not only to produce the beverage or broth, but can also be used to stir the solution during extraction. When in the form of a straw or tube, the cylindrical member 42 may also be used to drink the beverage or broth. Of particular advantage, further flavoring of the beverage or broth may occur as the solution is drawn up through the straw.

The cylindrical member 42 can have any suitable length, such as from about 4 inches to about 30 inches, such as from about 4 inches to about 24 inches.

The cylindrical member 42 can be formed in various ways. In one embodiment, for instance, the cylindrical member 42 can include an infusion portion 52 connected to a handle portion 54. The handle portion 54 is for handling the cylindrical member 42 without touching the reconstituted material. The handle portion 54 can comprise any suitable material. For instance, the handle portion 54 can be formed by coating or covering the reconstituted material. For instance, the reconstituted material can be coated with a polymer, such as a film-forming solution. Alternatively, the reconstituted material may be covered with a paper material. In still another embodiment, the handle portion 54 can be made exclusively from a different material and attached to the infusion portion 52. For instance, the handle portion 54 can be made from a plastic or paperboard material, such as materials that have been used conventionally to make straws.

In one embodiment, one or more of the cylindrical members can be packaged in a dispenser 56. In the embodiment illustrated in FIG. 19D, for instance, a plurality of the infusion products 40 can be placed in the carton 56 for use by a consumer. The carton or package 56 can include a perforated portion 58 that can be removed for access to the product within the container. The package 56 can be made from paper, a paperboard, or from a plastic material, such as a rigid plastic or a flexible plastic film.

Referring to FIGS. 19E and 19F, further embodiments of infusion products made in accordance with the present disclosure are shown. In the embodiments illustrated in FIGS. 19E and 19F, the infusion product 60 includes a layer or sheet of fibrous plant product that, in one embodiment, has been treated with a plant extract in accordance with the present disclosure and the above description. As shown in the figures, the layer of fibrous plant product 62 can have any suitable shape. In FIG. 19E, for instance, the layer of fibrous plant product is in the shape generally of a rectangle. In FIG. 19F, on the other hand, the layer of fibrous plant product 62 is more in the shape of a square. As shown, each infusion product 60 includes a reinforced area 64. The reinforced area 64 can be produced by laminating or attaching a material to the layer of fibrous plant product. The reinforced area, for instance, can be made by laminating a material, such as a fabric, a plastic film, a woven fabric, or a knitted fabric to the layer of fibrous plant product. Alternatively, the reinforced area 64 can be produced by applying a coating to one or more sides of the layer of fibrous plant product 62.

The reinforced area 64 includes an opening 66 for engaging a rod member 68 for positioning the infusion product 60 into a cup or mug 70. The opening 66 can comprise an aperature, a slot, a notch, or any suitable channel formed into the reinforced area 64.

The rod member 68 can have any suitable shape. In FIG. 19E, for instance, the rod member 68 has a straight and linear shape. In the embodiment of FIG. 19F, on the other hand, the rod member 68 is in the shape of a ring. In one embodiment as shown in FIG. 19F, the ring-shaped rod member can include an opening for being placed over the edge or lip of a cup or mug 70.

In one embodiment, the rod member 68 as shown in FIGS. 19E and 19F can be constructed similar to the cylindrical member 42 illustrated in FIG. 19D. For instance, the rod member 68 can be made from a reconstituted material and can include a handle portion 72.

Figure 19H:
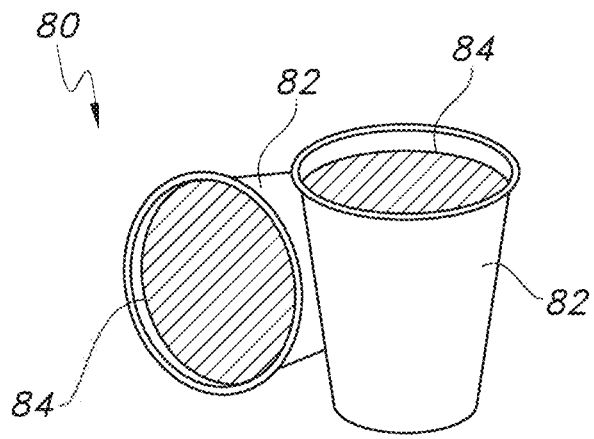

Still another embodiment of an infusion product 80 is shown in FIG. 19H. In FIG. 19H, a cup 82 is illustrated that includes a lining 84. Lining 84 can be integral with the cup 82 or can be a layer placed against or adhered to the cup 82. In accordance with the present disclosure, the lining 84 is formed from a reconstituted material made in accordance with the present disclosure. For instance, the lining 84 can be made from a layer of fibrous plant product that has been treated with a plant extract. The cup 82 can be disposable or can be made from a more permanent material, such as a ceramic. The lining 84 is generally for a single time use. In one embodiment, the lining can be sold separately from the cup 82. Thus, when a beverage or broth is desired, the lining 84 can be inserted into the cup and contacted with a liquid, such as water.

Figure 19I:
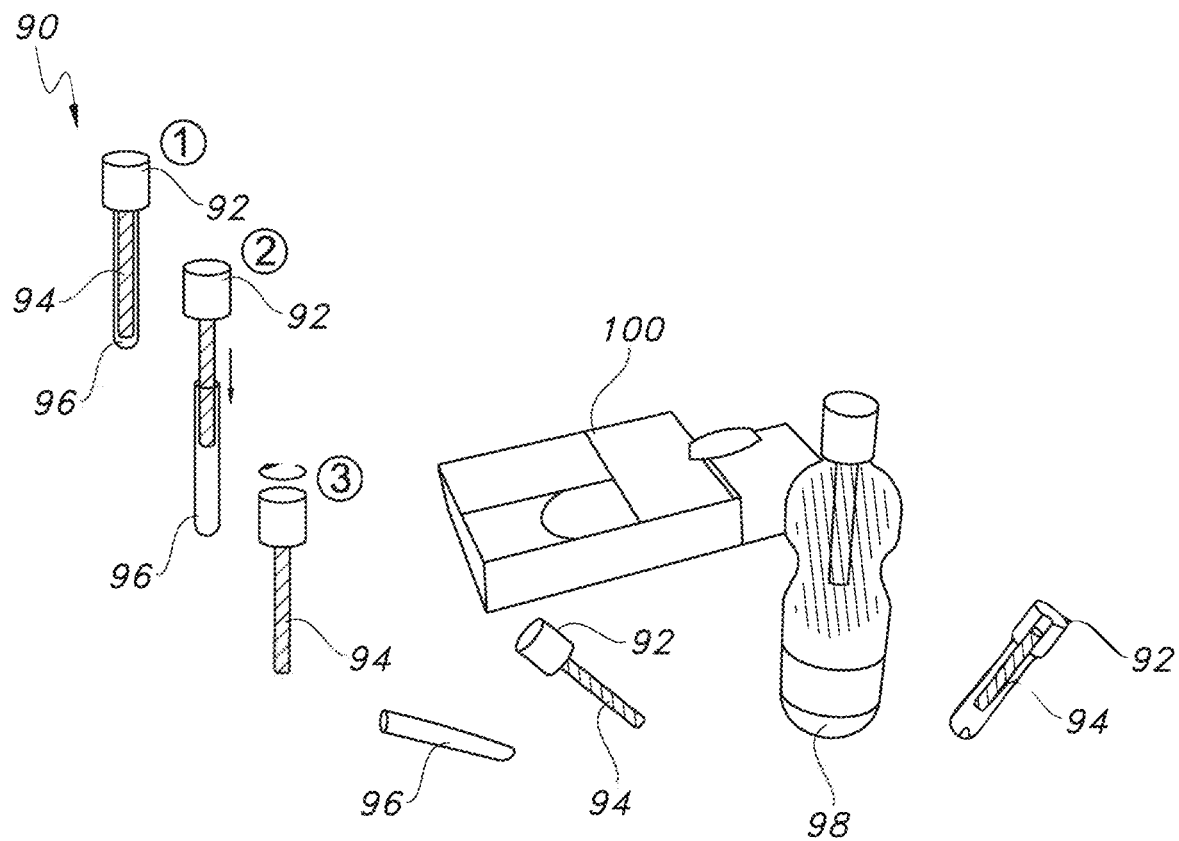

Referring to FIG. 19I, still another embodiment of an infusion product 90 made in accordance with the present disclosure is shown. In the embodiment illustrated in FIG. 19I, the infusion product 90 includes a cap member 92 connected to an infusion member 94. The infusion member 94 can have any suitable shape and geometry. In the embodiment illustrated, for instance, the infusion member 94 is in the shape of a cylinder. The infusion member 94, for instance, can have the same construction as the cylindrical member 42 shown in FIG. 19D. Alternatively, the infusion member may comprise a plurality of infusion filaments, such as the infusion filaments 38 as shown in FIG. 19B. The infusion member 94 is formed from the reconstituted material made in accordance with the present disclosure and may comprise a layer or rod of fibrous plant product that has been treated with a plant extract.

As shown in FIG. 19I, the infusion product 90 can further include a sheath 96. The sheath 96 is for protecting the infusion member 94 prior to use. In order to use the infusion product 90, the sheath 96 is removed from the infusion member 94. The cap member 92 is then used to secure the infusion member 94 onto a bottle 98, such as a water bottle. In one embodiment, the water bottle 98 can then be shaken in order to allow an extraction to occur for producing a broth or beverage.

As shown in FIG. 19I, a plurality of the infusion products 90 can be contained within a carton or package 100 for purchase and use by the consumer.

Figure 19J:
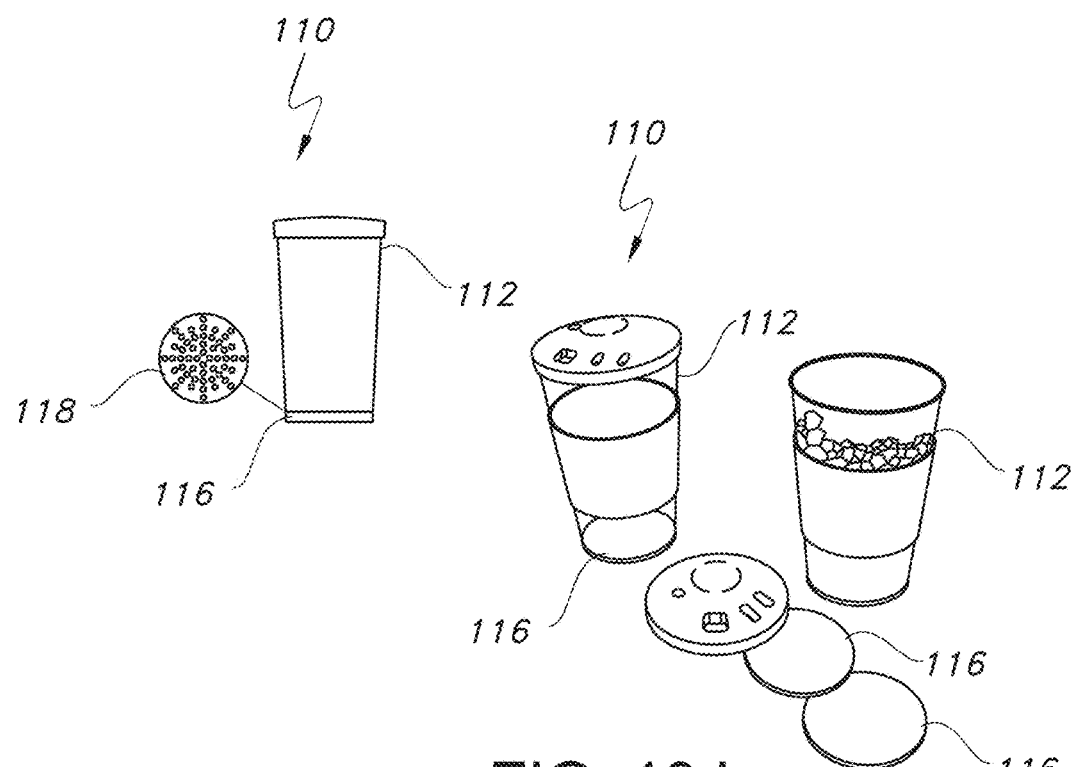

Referring to FIG. 19J, still another embodiment of an infusion product 110 made in accordance with the present disclosure is shown. In the embodiment illustrated in FIG. 19J, the infusion product 110 comprises a shaker that is designed to produce a beverage, particularly a cold beverage such as iced tea. The infusion product 110 includes a cup or tumbler 112. The cup or tumbler 112 includes a top 114. The top 114 can be liquid tight such that the cup or tumbler can be filled with a liquid, covered with the top, and shaken without any liquid release or leaking. The top 114, for instance, may include a gasket made from an elastomeric material to ensure a liquid tight seal. The top 114 can fit over the cup 112 using threads or can have a tension fit.

In accordance with the present disclosure, the cup or tumbler 112 is used in conjunction with an infusion member 116. The infusion member 116 can be made from the reconstituted material in accordance with the present disclosure and may comprise a fibrous plant product that has been treated with a plant extract. The infusion member 116 can have any suitable shape. In the embodiment illustrated in FIG. 19J, for instance, the infusion member 116 is in the shape of a disk. It should be understood that the infusion product 110 can include a single infusion member 116 or can include multiple infusion members. The infusion member 116 illustrated in FIG. 19J is configured to have a diameter that is slightly smaller than the diameter of the cup or tumbler 112. In this regard, the infusion member can be placed at the bottom of the cup or tumbler and generally match the diameter of the inside wall of the cup or tumbler.

Optionally, the infusion product 110 can include a baffle 118. As shown in FIG. 19J, the baffle can be circular in shape and generally have approximately the same diameter as the cup or tumbler. The baffle 118 can comprise a perforated base. The baffle 118 is designed to fit over the infusion member 116 to form a reservoir for the infusion member 116 at the bottom of the cup or tumbler.

In order to produce a beverage, the infusion member 116 can be placed in the cup or tumbler 112. If desired, the baffle 118 can be placed over the infusion member 116. The cup or tumbler 112 can then be filled with a liquid, such as water. The top 114 can be placed on the cup or tumbler and the entire assembly can be shaken to form a beverage.

In one particular embodiment, after the infusion member 116 and baffle 118 are placed in the cup or tumbler 112, the cup or tumbler can be filled with fresh water and possibly ice cubes. The infusion member 116 can comprise a layer of fibrous plant product comprising a tea. In this manner, the infusion member 116 can be used to produce a tea beverage, such as iced tea.

In one embodiment, instead of shaking the infusion product 110, the cup or tumbler can be filled with water and placed into a refrigerator with no ice cubes. Once refrigerated so that the water obtains a desired temperature, the cup or tumbler can be removed from the refrigerator and shaken to produce iced tea.

Figure 19K:
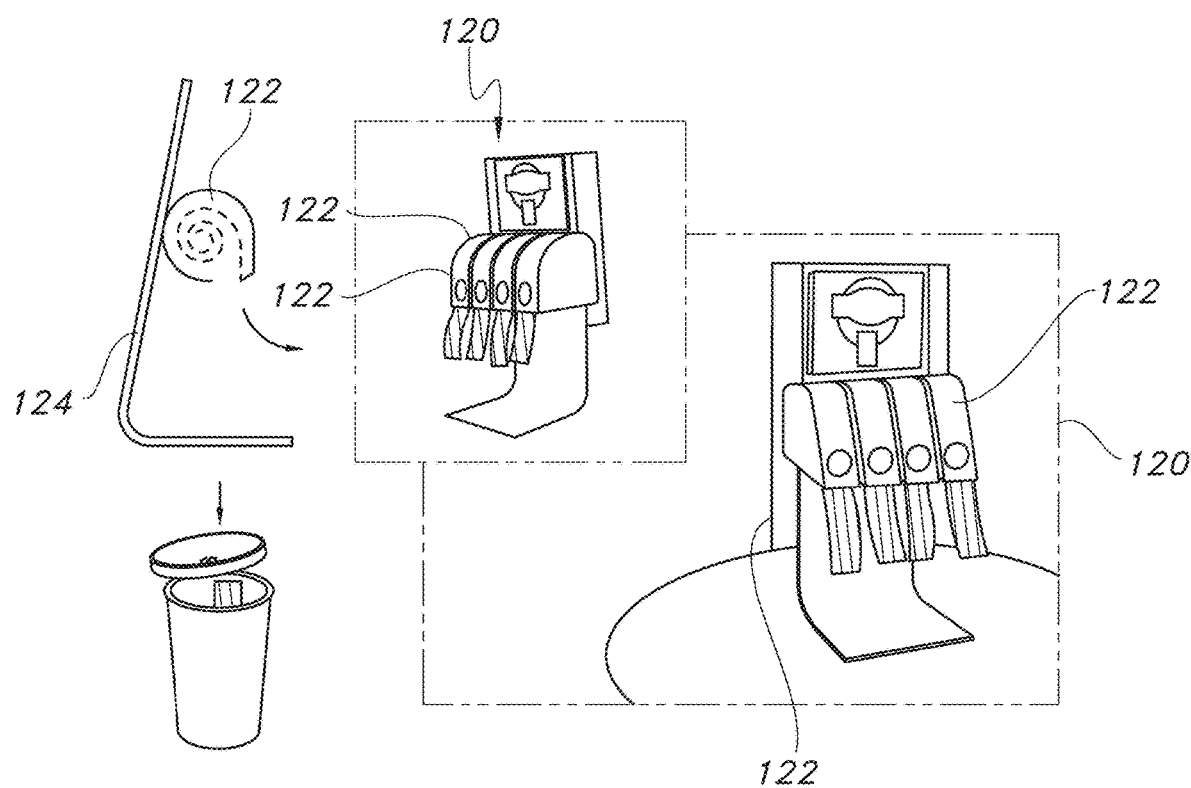

Yet another embodiment of an infusion product 120 made in accordance with the present disclosure is illustrated in FIG. 19K. The infusion product 120 illustrated in FIG. 19K includes a plurality of infusion product dispensers 122. The infusion product dispensers 122 can be configured similar to the infusion product dispenser illustrated in FIG. 19A, illustrated in FIG. 19C, or illustrated in FIG. 19G. Each infusion product dispenser can contain a reconstituted material in accordance with the present disclosure. In this embodiment, each infusion product dispenser can contain a different product. For instance, each infusion product dispenser may contain an infusion member or strip made from a different type of tea or herbal tea. In this manner, a consumer has a variety of teas to select from in producing a beverage.

As shown in FIG. 19K, the infusion product dispensers 122 can be mounted onto a frame 124.

Figure 21:
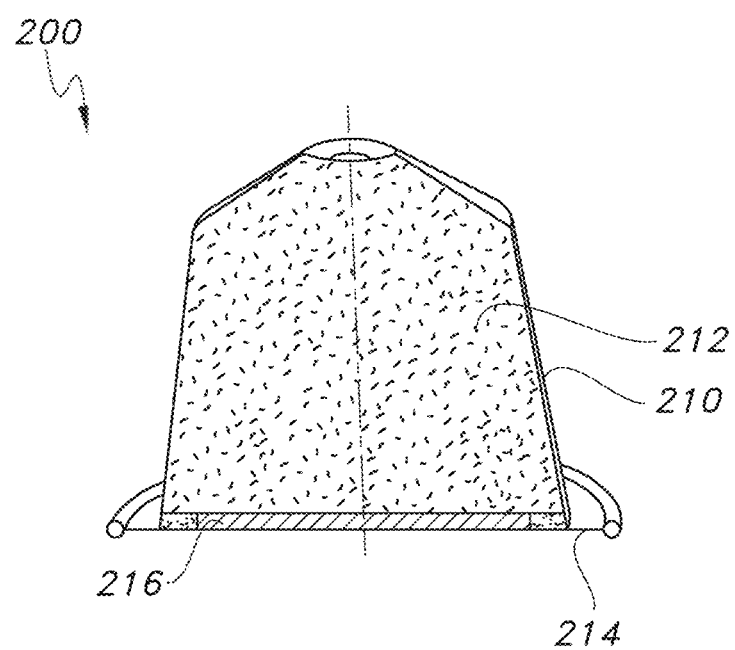
FIG. 21 shows a cross-sectional view of one embodiment of an infusion product made in accordance with the present disclosure that comprises a capsule containing reconstituted material.

Referring to FIG. 21, still another embodiment of an infusion product 200 made in accordance with the present disclosure is shown. In this embodiment, the infusion product 200 comprises a capsule 210 containing the reconstituted material 212 of the present disclosure. The infusion product 200 is for producing a broth or beverage. In one embodiment, for instance, the reconstituted material 212 comprises a tea or herbal tea that can be used to produce a tea beverage. The infusion product 200 as shown in FIG. 21 is particularly well suited to be used in connection with conventional single capsule coffee brewing machines.

Single chamber beverage capsules such as the one shown in FIG. 21 have a single chamber defined by a plastic or aluminum body. As shown, the chamber contains the reconstituted material 212 for producing a beverage in a high pressure beverage preparing machine. Hot water is injected under pressure by the beverage preparing machine into the single chamber containing the reconstituted material. As the pressure within the chamber increases, a capsule cover 214 is forced against raised projections in a capsule holder to the point that the projections penetrate the cover 214 so that the beverage flows through the cover and into a user's cup.

One advantage of single serve beverage capsules is that each serving contains a fresh supply of ingredients. The freshness of the ingredients can be preserved through a modified atmosphere packaging process where the air within the capsule is modified such as by replacing the air with inert gas prior to sealing. The inert gas, for instance, may comprise nitrogen.

The capsule 210 illustrated in FIG. 21 includes a body that can be made of aluminum and/or plastic and may be relatively stiff to prevent collapse, especially when the top is being perforated within the beverage production machine. The top 214 can be made from a material capable of being pierced during production of a beverage. For instance, the top 214 can be made from a foil or a plastic film.

Optionally, the infusion product 200 can include a filter 216 positioned between the reconstituted material 212 and the top 214. The filter 216 can be made from, for instance, a 3-dimensional open cell structure such as a foam material. The filter 216 is permeable to liquids but impermeable to solid particles. The filter 216 can be used to prevent the reconstituted material from entering the beverage.

Of particular advantage, however, capsules can be made according to the present disclosure that do not contain the filter 216. In particular, the reconstituted material 212 can be in the form of pellets, sheets, fibrous layers, and the like. For instance, the reconstituted material 212 can comprise particles or forms that have sizes greater than 100 microns, such as greater than 500 microns, such as greater than 1,000 microns. By using larger sized particles or forms, the use of the filter 216 can be avoided.

The amount of reconstituted material 212 contained in the capsule can vary. In general, the capsule can contain the reconstituted material in an amount greater than about 1 gram, such as greater than about 3 grams, such as greater than about 5 grams, such as greater than about 7 grams. The capsule can contain the reconstituted material in an amount less than about 20 grams, such as less than about 15 grams, such as less than about 10 grams, such as even less than about 5 grams.

The reconstituted material of the present disclosure is well suited to making teas. In the case of teas or other compositions for use in making beverages, the consumer does not need to use a conventional filter paper (tea bag) for preparing the infusion. Specifically, no other accessory is required (instead of water and a cup or a glass) for making the infusion.

In one embodiment, the composition offers a high level of biodegradability, for example by allowing the composting of tea bags.

In sum, the reconstituted plant products of the invention provide several benefits and advantages, such as

- the provision of products with higher infusion yield and infusion speed (both with boiling water and water at room temperature);
- the provision of a new format to infuse beverages without the need of packages and accessories;
- the provision of a preferably dispersible and biodegradable product;
- the ability to adjust the content of active ingredients (such as polyphenols, essential oils and the like) to provide a consistent composition;
- the ability to adjust (reduce) the content of undesired constituents (such as pesticides, caffeine, nicotine, aluminum, heavy metals, and the like);
- the ability to provide new sensory characteristics (such as adjusting intensity of flavor, mixture of various plants and the like); and
- reduction of the bacterial load during the manufacturing process.

The following examples further describe and demonstrate embodiments that are within the scope of the present invention. The examples are given solely for the purpose of illustration, and are not to be construed as limitations of the present invention since many variations thereof are possible without departing from its spirit and scope.

EXAMPLES

Example 1

A tea product was made according to the following method: A black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the samples were then refined in a Valley beater at 1.4% consistency for 10 minutes. After refining, cellulosic fibers (a blend of abaca, hardwood and softwood pulps, with the respective ratios 60/10/30) were added to the tea fibrous residue with a tea fiber/woodpulp ratio of 5 to 1 in weight in order to make hand sheets. The aqueous portion was concentrated in an evaporator to a solid concentration of 50% and then coated on a hand sheet on a manual size-press. The soluble level is typically between 27 and 37% in dry finished product. In example 1, soluble level of the reconstituted tea was approx. 27%, which is the soluble content of conventional tea used as the starting material of the experiment. The coated hand sheets were dried on a plate dryer.

The product obtained in this example (reconstituted tea; "B20" sample in the form of discs, containing a coating made by impregnation with tea extract) was tested for its properties in preparing tea and compared to a conventional tea product in tea bags. Both products were used to make tea, and the optical density of the solution (tea) was measured at 274 nm. For both samples, the total infusion time in hot water (90° C.) was 2.5 minutes which usually corresponds to consumer habit. Same weights of tea material and identical experimental conditions were used: a beaker containing 200 ml water (ref. Cristaline) was heated at 90° C. At T=0, ie. upon start of the experiment, heating was stopped and the tea bag was immersed into water. A rotary magnet was used to homogenize the content of the beaker during the entire experiment.

Samples of water were taken regulary, every 30 seconds and up to 3 minutes. Then, the optical density of the sample was determined using a spectrophotometer at the wavelength of 274 nm (maximum absorption of caffeine). The reference/blank test was run with a sample of clear water (Cristaline) heated at 90° C.

The optical densities measured (after 3 minutes of infusion) for the reconstituted tea product were 0.69, whereas for the conventional tea bag 0.63 was measured. The result is graphically shown in FIG. 1. Thus, for reconstituted tea (B20), a higher infusion rate of solubles was obtained as with the conventional product in tea bags. The extraction ratio in this test was +10% as compared to the conventional product in tea bags. The reconstituted tea enabled a more efficient infusion (100% solubles are extracted from the plant); using the same amount of material, more solubles could be released from reconstituted tea than from natural tea.

Similar results were obtained with different infusion times, or when reconstituted tea was compared to tea in loose form. Also, similar results were obtained with reconstituted products made from herbs as compared to conventional herbal tea products.

Example 2

The product of example 1 (B20) was used to determine the infusion rate as compared to conventional tea in tea bags.

Figure 2:
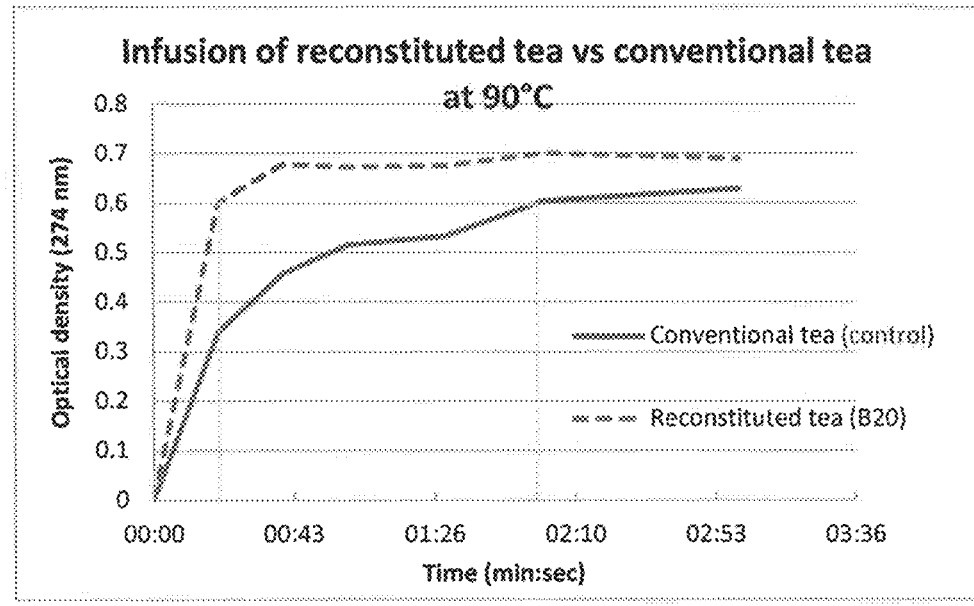
FIG. 2 is a graph showing total infusion time in hot water (90° C.) for an impregnated tea product (fiber-web made of non soluble tea particles impregnated with soluble tea portion) as compared to a conventional tea in the form of a tea bag.

The optical densities were measured over time. The experimental set-up was identical to example 1. For the reconstituted tea product, an optical density of 0.6 was reached within 20 seconds from contacting the same with water, whereas about 2 minutes were required to obtain the same optical density using the conventional tea bag. The result is graphically shown in FIG. 2.

The example demonstrates that the reconstituted tea product provides faster infusion than conventional tea in tea bags.

Similar results were obtained when reconstituted tea was compared to tea in loose form. Also, similar results were obtained with reconstituted products made from herbs as compared to conventional herbal tea products.

Example 3

Figure 3:
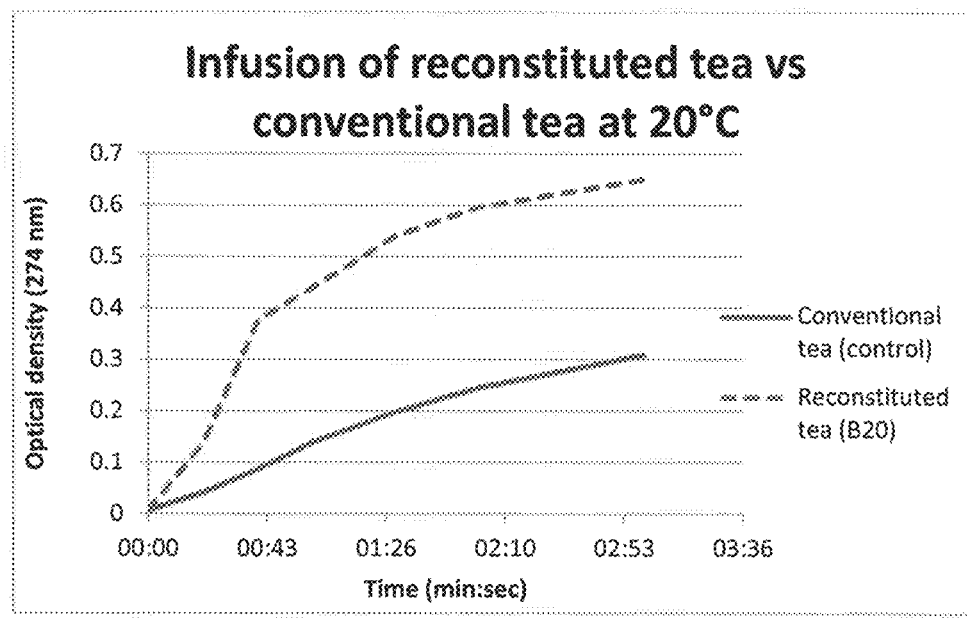
FIG. 3 is a graph showing total infusion time in cold water (20° C.) for an impregnated tea product (fiber-web made of non soluble tea particles impregnated with soluble tea portion) as compared to a conventional tea in the form of a tea bag.

The product of example 1 (B20) was used to determine its infusion properties at different temperatures as compared to conventional tea in tea bags As in example 2, the optical densities were measured over time. The experimental set-up was identical to example 2, except for the fact that water at room temperature (20° C.) was used instead of hot water (90° C.). For the reconstituted tea product, an optical density of 0.3 was reached within about 30 seconds (0.6 within about 2 minutes) from contacting the same with water, whereas the conventional tea bag required about 6 times longer to provide the optical density of 0.3. The result is graphically shown in FIG. 3.

The example demonstrates that even in cold water the reconstituted tea product provides faster infusion than conventional tea in tea bags. At 20° C., the extraction ratio after 3 minutes of infusion is much better than standard product (+100%), Also, the extraction ratio of the reconstituted tea material at 20° C. is similar to the the extraction ratio at 90° C.

Similar results were obtained when reconstituted tea was compared to tea in loose form. Also, similar results were obtained with reconstituted products made from herbs as compared to conventional herbal tea products.

Example 4

The following example demonstrates that the delivery of solubles and active ingredients can be easily adjusted in the manufacturing process (either decreased or increased as compared to a given standard).

As control, a conventional tea was used containing solubles in an amount of 26% (w/w). The soluble content was measured by determining the weight of a given sample before and after extraction. In a separate experiment, a portion of the same tea was subjected to a manufacturing process similar to example 1. The amount of solubles was adjusted in three different runs to 5% (w/w; decreased level), to 26% (w/w; standard level) and to 50% (w/w; increased level) by adjusted the coating ratio during impregnation.

The experiment demonstrates that the reconstituted product can be used to provide a consistent, standardized delivery level of soluble/active ingredients as compared to the natural products that generally show an inherent variability.

Example 5

Following the method disclosed for the product of example 1 (B20), similar products were obtained and tested. In these tests, different reconstituted tea products, i.e. reconstituted material constituted by the base web impregnated with the solubles portion of the original material, were produced and compared to conventional tea, either in loose form or in the form of tea bags. The reconstituted tea products varied in the solubles coating ratio, i.e. the amount of solubles coated onto the base web of reconstituted tea (dry basis weight of reconstituted plant material in g/m$^2$).

The following products were prepared and tested:

| Sample # | Description | Format | Dry basis weight | Amount of solubles (=coating ratio for reconstituted samples) |
|---|---|---|---|---|
| 1 | Original vegetal, unwrapped | Loose | na | Around 30% |
| 2 | The same vegetal as above but in tea bag (same plant and same origin as 1) | Tea bag (double chamber) | na | Around 30% |
| 3 | Standard reconstituted vegetal (same plant and same origin as 1 & 2) ie new delivery device | disks | Standard (100 gsm) | Same as original vegetal (30%) |
| 4 | Adjusted reconstituted vegetal (same plant and same origin as 1 & 2) | disks | standard | Decreased vs standard (20%) |
| 5 | Adjusted reconstituted vegetal (same plant and same origin as 1 & 2) | disks | standard | Increased vs standard (50%) |
| 6 | Adjusted reconstituted vegetal (same plant and same origin as 1 & 2) | disks | Decreased vs standard (60 gsm) | Same as original vegetal (30%) |

Specifically, sample #3 was compared with samples #1 and #2; sample #3 was compared with samples #4 and #5; and sample #3 was compared with sample #6.

The comparison of the properties of the products similar to the experiments performed in examples 1 to 4 confirm the results in examples 1 to 4, namely that reconstituted tea provides a better ratio of extraction and faster extraction, even at low temperature (water at room temperature) and allows to adjust the amount of solubles active ingredients realeased upon infusion.

Example 6

Tea bags were made from tea material, which was mixed in various batches with a blend of cellulose fibers (abaca, hardwood and softwood pulps, with the respective ratios: 60/10/30). As in example 1: a black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the samples were then refined in a Valley beater at 1.4% consistency for 10 minutes. After refining, cellulosic fibers (a blend of abaca, hardwood and softwood pulps, with the respective ratios: 60/10/30) were added to the tea fibrous residue at various levels in order to prepare the different samples and make hand sheets. Hand sheets were later dried on a plate dryer.

It is possible to make tea bags from a fiber web produced with an adjustable proportion of tea fibers or herb fibers (from 5% to 80% of the total weight), mixed with cellulosic and/or synthetic fibers. The proportion of tea or herb fibers can be distinctively high.

During the first trial, the ratio of tea/cellulosic fibers was 40/60 (w/w); in a second trial the ratio was 60/40 (w/w) and in a third trial, the ratio was 80/20 (w/w). The fibrous web used for making the tea bags was not impregnated but the tea bags were filled with tea (taken from conventional tea bags). Their infusion performance was compared to conventional tea bags containing the same amount of tea. The measurements were similar to examples 1 and 2.

Figure 4:
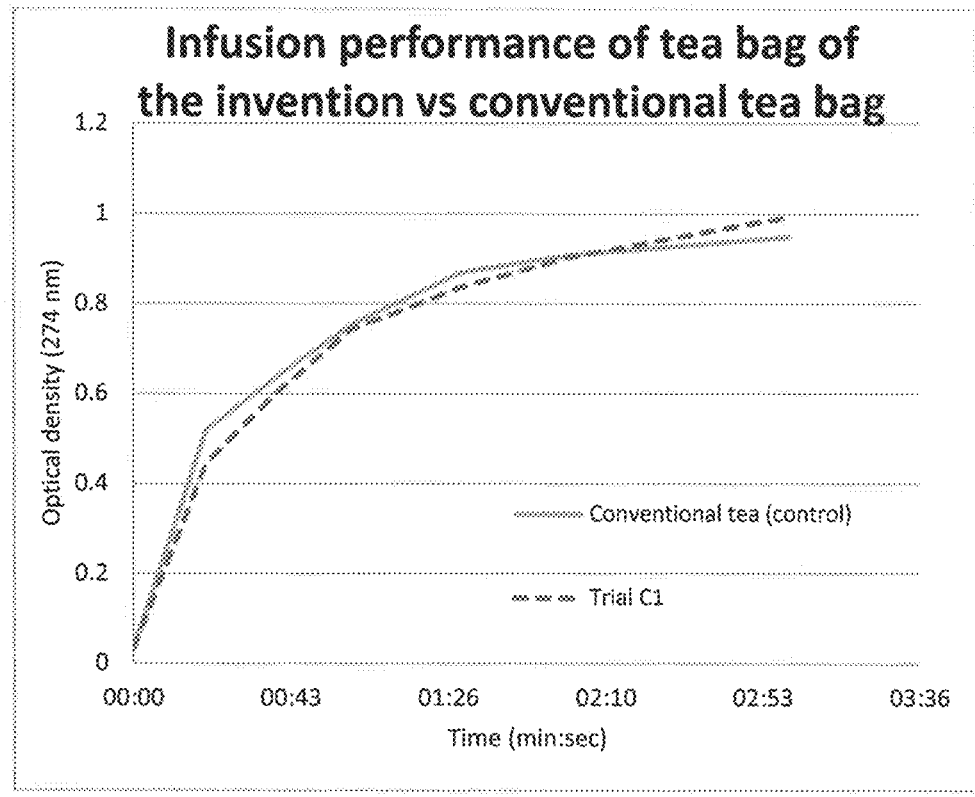
FIG. 4 is a graph showing infusion performance of a tea bag of the invention filled with conventional tea as compared to the infusion performance of a standard cellulosic tea bag filled with conventional tea.

The infusion performance of the sample corresponding to the 80/20 ratio (Trial C1) matched with the infusion performance of conventional cellulosic tea bags (control) as measured by optical density. The result is graphically shown in FIG. 4.

Example 7

In another trial, the fiber web used for making the tea bags of example 7 was impregnated with tea extract obtained in the extraction step coming from starting material. The tea bags were additionally filled with tea. The amounts of coating varied from 5% to 50% of the total weight.

In separate tests, fiber webs were made from tea (*Camellia sinensis*) or herbs used for producing herbal teas.

Infusion performance was measured and compared to conventional tea bags/herbal tea bags containing the same amount of tea/herbal tea. The measurements were similar to examples 1 and 2.

Again, more solubles were realeased, and infusion rates were faster for the reconstituted, impregnated tea bags than for the conventional tea bags due to the additional release of tea soluble from the coating, in addition to natural infusion coming from the tea which is contained in the bag. The additional delivery of solubles provides a distinctive stronger taste.

In one trial, an tea bag was made from tea, impregnated with tea extract as described above in this example. In infusion tests using water at 90° C., the product released 35% (w/w) tea solubles into the water.

Example 8

In one experiment, two different products were produced: product C1 in the form of a tea bag, containing about 5% solubles (w/w), with a dry basis weight of approx. 120 g/m$^2$ (w/w) and product B20 in the form of a tea bag, containing about 5% solubles (w/w), with a dry basis weight of approx. 60 g/m$^2$ (w/w). The tea bags were not filled with tea.

Figure 5:
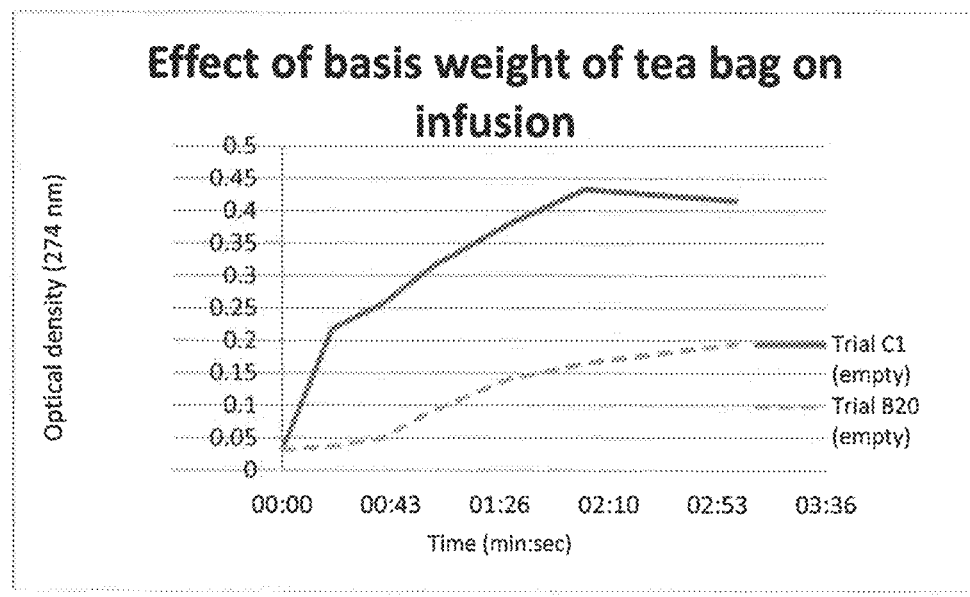
FIG. 5 is a graph showing infusion performance of a tea bag of the invention at a basis weight of 120 g/m$^2$ as compared to the infusion performance of a tea bag of the invention at a basis weight of 60 g/m$^2$. None of them have been filled with conventional tea.

Infusion performance under identical conditions was measured and compared for samples C1 and B20 similar to examples 1 and 2. The results which are graphically shown in FIG. 5 demonstrate that the release of tea solubles can be also driven by the basis weight of the finished product.

Example 9

Example 1 described above was repeated with the additional use of a wet strength agent (here: cationic polyamide amine resin), in order to reduce potential degradation of some of the reconstituted material in water. The wet strength agent was added to the fibrous portion.

A tea product was made according to the following method: A black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. The soluble level is typically between 27 and 37% in dry finished product. In this example, soluble level of the reconstituted tea was approx. 27%, which is the soluble content of conventional tea used as the starting material of the experiment. The coated hand sheets were dried on a plate dryer.

Infusion trials were run in hot water (approx. 90° C.) and product with wet strength agent showed less degradability into water than same material without agent.

Figure 6:
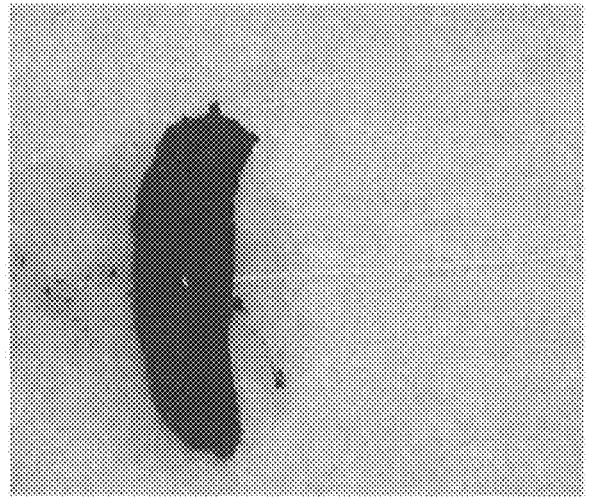
FIG. 6 shows reconstituted tea in one example without the use of a wet strength agent after 3 mins of infusion. The photograph shows that material is degraded.

FIG. 6 shows reconstituted tea in one example without the use of a wet strength agent after 3 mins of infusion. The photograph shows that material is degraded.

Figure 7:
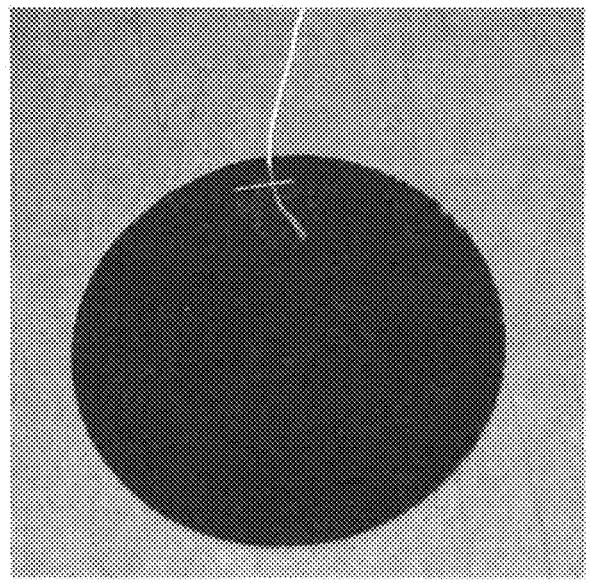
FIG. 7 shows reconstituted tea in this example with the use of a wet strength agent after 3 mins of infusion. The photograph shows that the material is substantially undegraded.

FIG. 7 shows reconstituted tea in this example with the use of a wet strength agent after 3 mins of infusion. The photograph shows that the material is substantially undegraded.

Example 10

In order to determine the effect of reconstituted tea soluble content and the dry basis weights on the infusion profile, a tea product was made according to the following method: A black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. The soluble level is typically between 27 and 37% in dry finished product. In this example, the following products were prepared:

Product A: soluble level of the reconstituted tea was 22%. Which is the soluble content of conventional tea used as the starting material of the experiment. Dry basis weight of the material was 70 grs per m² (dry basis);

Product C: soluble level of the reconstituted tea was 22%, which is the soluble content of conventional tea used as the starting material of the experiment. Dry basis weight of this material was 170 grs per m² (dry basis) which is 143% higher than A;

Product D: soluble level of the reconstituted tea was 38% which is 73% higher than A. Dry basis weight of D material was 170 grs per m² (dry basis) also The coated hand sheets were dried on a plate dryer.

The products (A, C and D) obtained in this example were tested for their properties in preparing tea and compared. Both products were used to make tea, and the optical density of the solution (tea) was measured at 2.74 nm. For all samples, the total infusion time in hot water (90° C.) was 5 minutes. Same weights of tea material (2.5 grs) and identical experimental conditions were used: a beaker containing 500 ml water was heated at 90° C. At T=0, ie, upon start of the experiment, heating was stopped and a tea strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 274 nm (maximum absorption of caffeine). The reference/blank test was run with a sample of clear water heated at 90° C.

Figure 8:
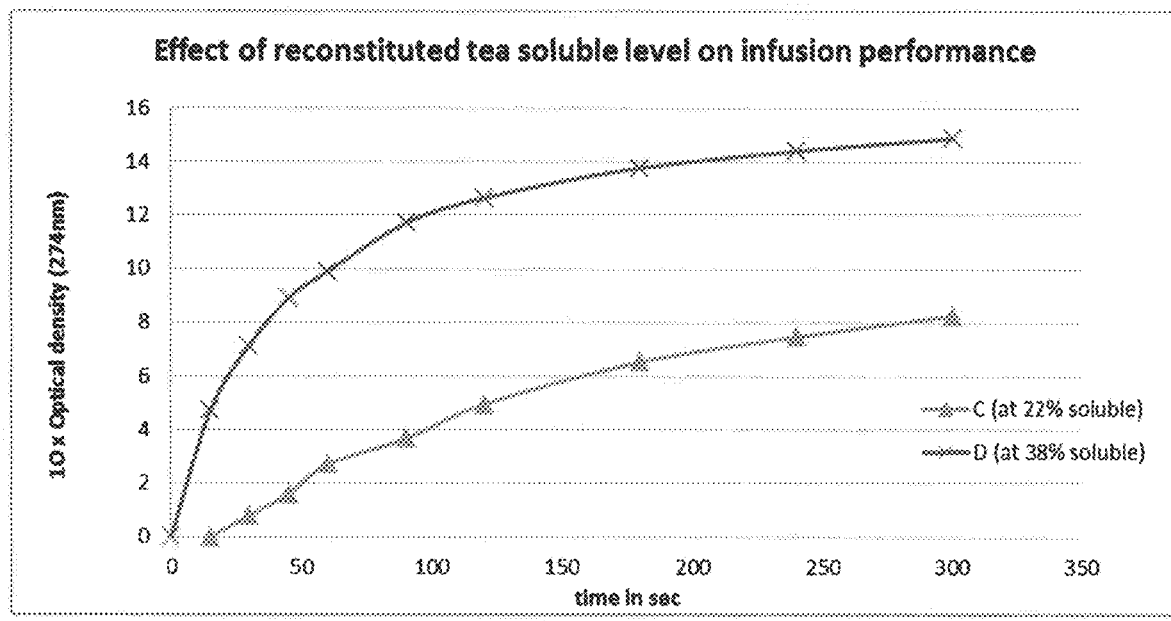
FIG. 8 shows a reconstituted material produced according to Example 10. Reconstituted tea (D-high soluble content) shows a higher infusion level of tea solubles than C (standard soluble level).
Figure 9:
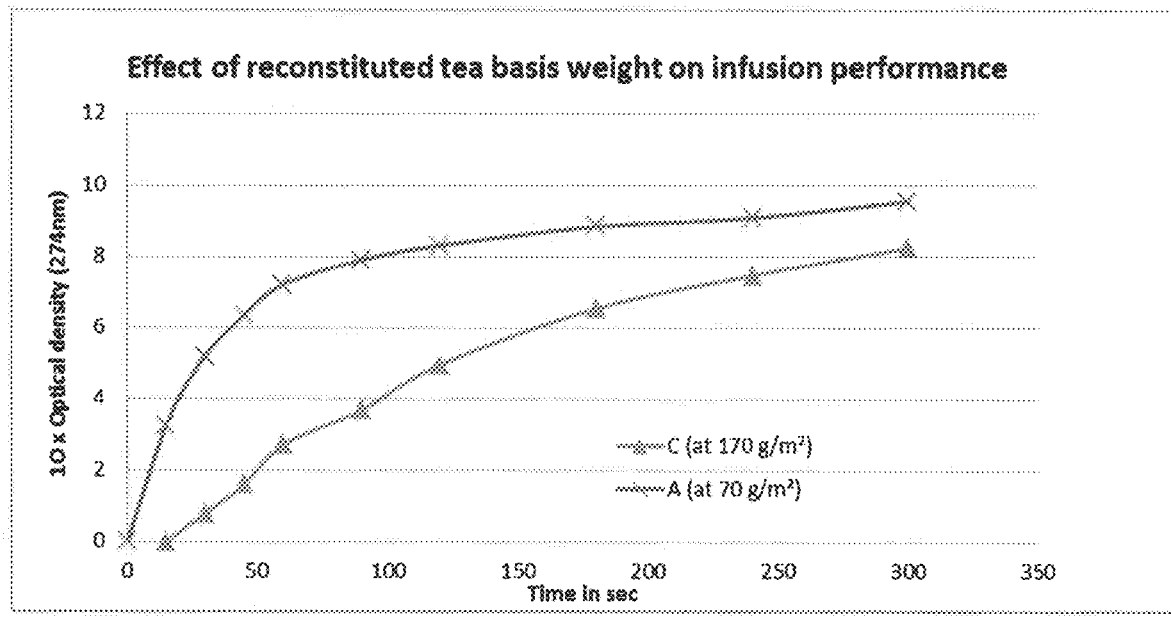
FIG. 9 shows a reconstituted material produced according to Example 10. Reconstituted tea A with a lower basis weight shows a faster infusion level of tea solubles than C.

The result is graphically shown in FIGS. 8 and 9.

FIG. 8: Reconstituted tea (D—high soluble content) shows a higher infusion level of tea solubles than C (standard soluble level). In order to reach an infusion level of 8.3 (expressed by 10× optical density at 274 nm), it takes 300 sec with sample C whereas only 40 sec are needed for D material (87% faste). Sensory evaluation performed by tea panel group also showed a stronger tea flavor and taste with D than with C after 5 mins infusion. This demonstrates that tea infusion taste can be adjusted thanks to soluble content of reconstituted tea material.

FIG. 9 shows that Reconstituted tea A with a lower basis weight shows a faster infusion level of tea solubles than C. Figures show that infusion rate of 8.3 (expressed by 10× optical density at 274 nm) is reached in 120 sec for A sample whereas 300 sec are needed for C. Infusion with A is 60% faster than with C. Actually, a lower basis weight for a given weight of material entails a more important contact surface which, at the end, improves infusion kinetics.

Example 11

In order to determine the effect of the reconstitution process on the green tea infusion sensory profile, a tea product was made according to the following method: a green tea (Sencha from China) was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes.

After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 36% extract content, which is the soluble content of the starting material of the experiment. The coated hand sheets were dried on a plate dryer.

Figure 10:
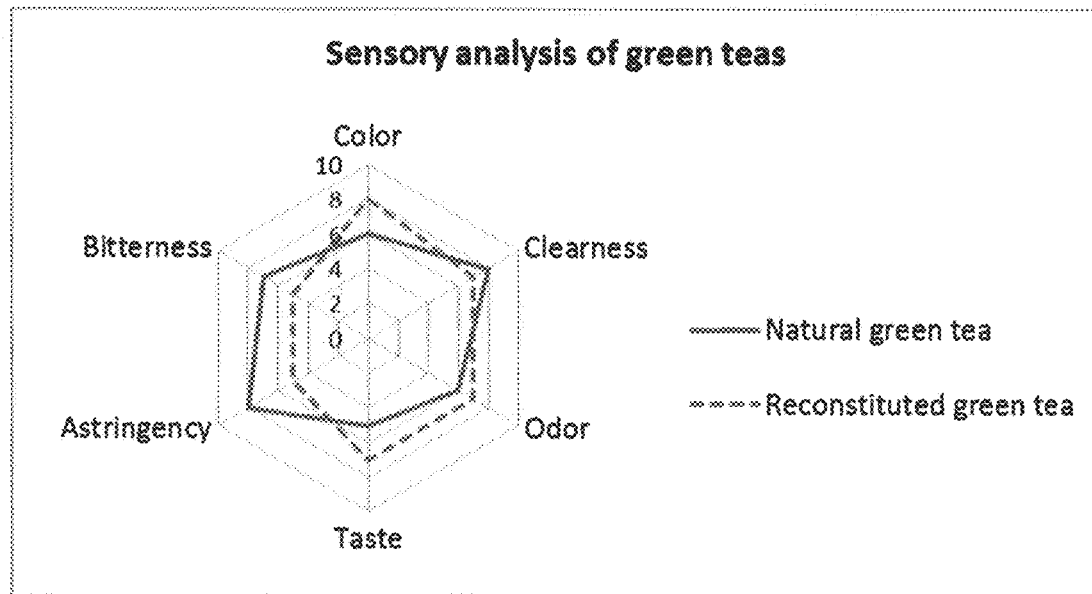
FIG. 10 shows the sensorial profile of reconstituted green tea and natural material.

The product obtained in this example was tested for its sensory properties and compared to natural tea material used for the experiment as described above. Both products were used to make tea. For all samples, the total infusion time in hot water (90° C.) was 5 minutes. Same weights of tea material (2 grs) and identical experimental conditions were used: a beaker containing 200 ml water was heated at 90° C. and tea materials were immersed into water. Then, after 5 minutes, sensory profile of both products was performed. The result is graphically shown in FIG. 10.

The experiment shows that the odor, color and taste are higher in the reconstituted tea than the natural material. However, astringency and bitterness are significantly lower in the reconstituted tea than natural material.

Example 12

Reconstitution of Rooibos Leaves

A reconstituted product was made according to the following method: Rooibos (*Aspalathus linearis*) was initially heated at 85° C. for 20 minutes with a rooibos/water ratio of 1 to 5 by weight. This was followed by an extraction step in a hydraulic press to separate the aqueous portion from the rooibos fiber portion. The recovered rooibos fiber portion was again heated at 85° C. for 10 minutes with a rooibos/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the rooibos fibrous residue with a rooibos fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 22% extract content, which is the soluble content of the starting material of the experiment. The coated hand sheets were dried on a plate dryer.

Figure 11:
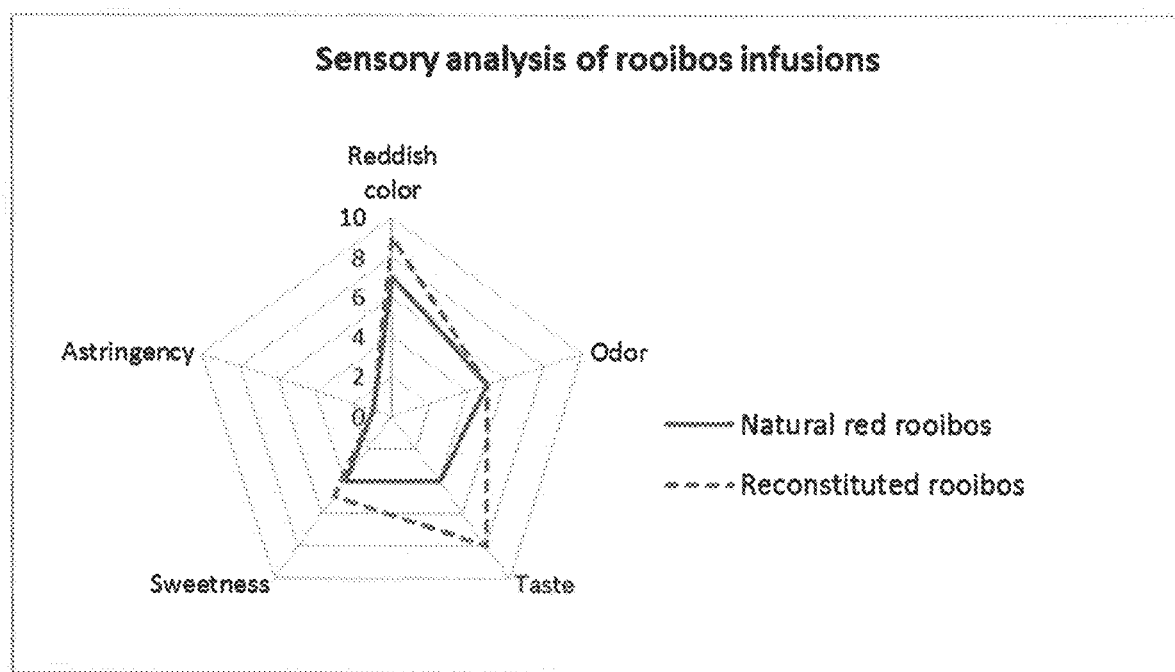
FIG. 11 shows the sensory analysis of reconstituted rooibos and reconstituted material (rooibos leaves).

The product obtained in this example was tested for its sensory properties and compared to natural rooibos material used for the experiment as described above. Both products were used to make a rooibos beverage. For all samples, the total infusion time in hot water (90° C.) was 5 minutes. Same weights of rooibos material (2 grs) and identical experimental conditions were used: a beaker containing 200 ml water was heated at 90° C. and rooibos materials were immersed into water. Then, after 5 minutes, sensory profile of both products was performed. The result is graphically shown in FIG. 11.

The experiment demonstrates that reconstituted rooibos tea shows a stronger taste than original material. Moreover, color is stronger.

The reconstituted rooibos obtained in this example and its original material were tested for their properties in preparing infusion and compared. Both products were used to make infusion, and the optical density of the solution was measured at 450 nm. For all samples, the total infusion time in hot water (90° C.) was 5 minutes. Same weights of materials (2.5 grs) and identical experimental conditions were used: a beaker containing 500 ml water was heated at 90° C. At T=0, ie. upon start of the experiment, heating was stopped and a reconstituted rooibos strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 450 nm (maximum absorption of lutein). The reference/blank test was run with a sample of clear water heated at 90° C.

Figure 12:
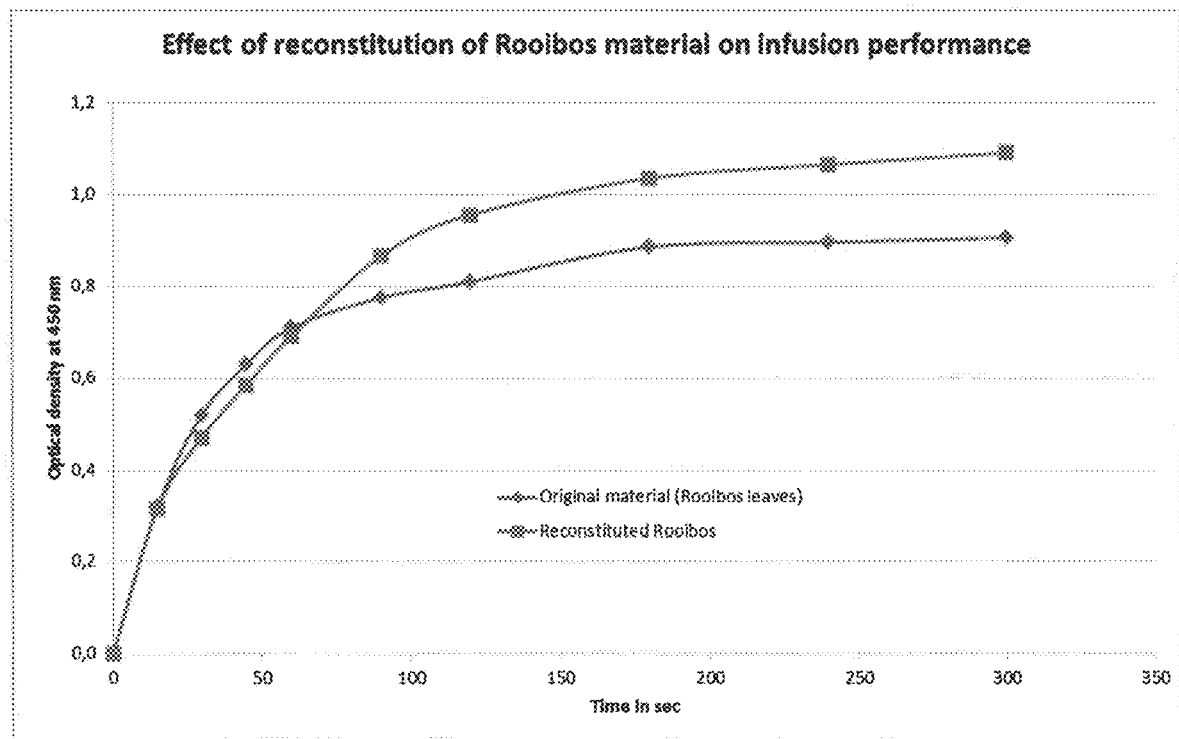
FIG. 12 shows the infusion performance of a reconstituted Rooibos material.

The infusion performance for reconstituted Rooibos material is graphically shown in FIG. 12. Infusions of rooibos products are comparable. However, it is demonstrated that reconstituted rooibos offers a more complete extraction. After 5 mins infusion, optical density of liquor made of reconstituted rooibos is 1.1 compared 0.9 for original material (+22%).

Example 13

Reconstitution of Thyme Leaves

A reconstituted product was made according to the following method: Thyme (*Thymus vulgaris*) was initially heated at 85° C. for 20 minutes with a thyme/water ratio of 1 to 5 by weight. This was followed by an extraction step in a hydraulic press to separate the aqueous portion from the thyme fiber portion. The recovered thyme fiber portion was again heated at 85° C. for 10 minutes with a thyme/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the thyme fibrous residue with a thyme fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 30% extract content, which is the soluble content of the starting material of the experiment. The coated hand sheets were dried on a plate dryer.

Figure 13:
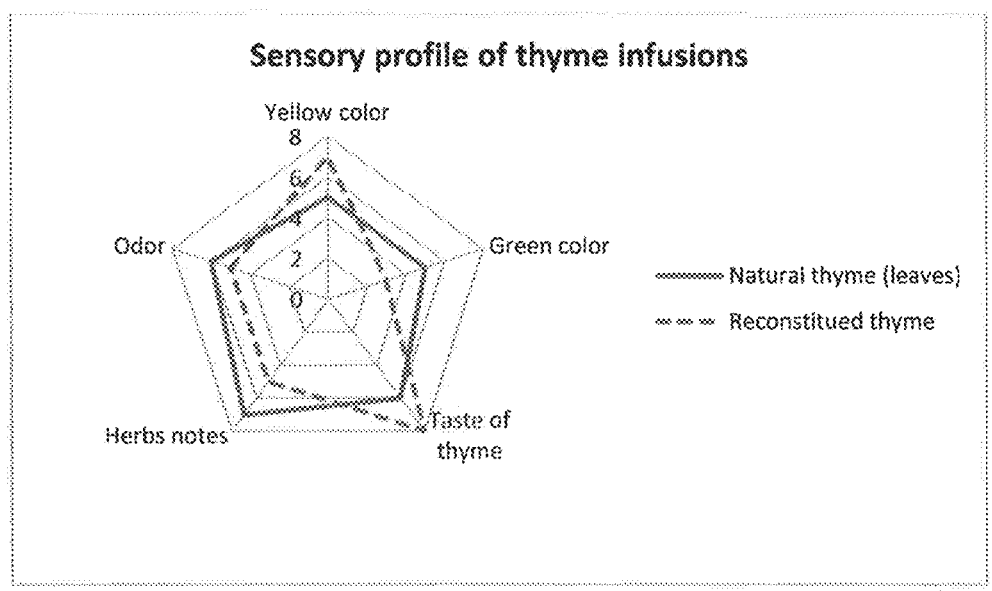
FIG. 13 shows the sensory profile of thyme leaves as compared to reconstituted thyme.

The product obtained in this example was tested for its sensory properties and compared to natural thyme material used for the experiment as described above. Both products were used to make a thyme beverage. For all samples, the total infusion time in hot water (90° C.) was 5 minutes. Same weights of thyme material (2 grs) and identical experimental conditions were used a beaker containing 200 ml water was heated at 90° C. and thyme materials were immersed into water. Then, after 5 minutes, sensory profile of both products was performed. The result is graphically shown in FIG. 13.

The experiment shows that that the color is rather yellow for the reconstituted thyme and rather green for the naturel leaves. Global odor and herbal notes are higher for the natural thyme. However, the taste of thyme is higher in the reconstituted material.

The reconstituted thyme obtained in this example and its original material were tested for their properties in preparing infusion and compared. Both products were used to make infusion, and the optical density of the solution was measured at 326 nm. For all samples, the total infusion time in hot water (90° C.) was 5 minutes. Same weights of materials (2.5 grs) and identical experimental conditions were used: a beaker containing 500 ml water was heated at 90° C. At T=0, ie. upon start of the experiment, heating was stopped and a reconstituted thyme strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 326 nm (maximum absorption of rosmarinic acid). The reference/blank test was run with a sample of clear water heated at 90° C. The result is shown in FIG. 14.

Figure 14:
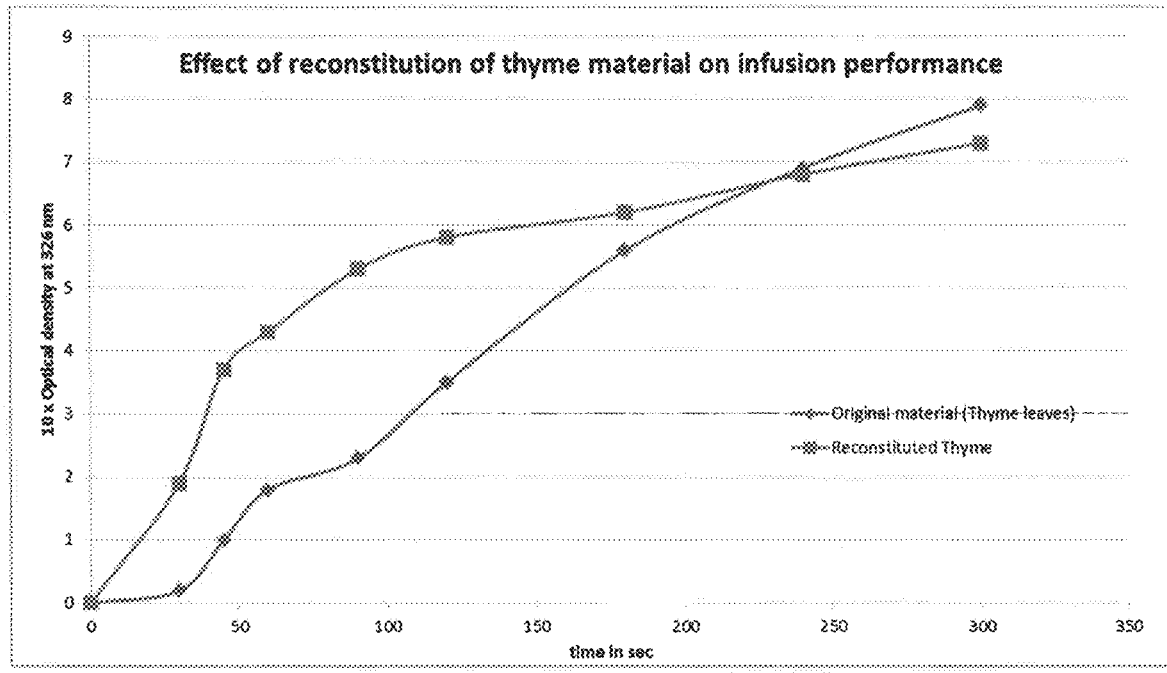
FIG. 14 shows the infusion performance of a reconstituted thyme material.

FIG. 14 shows that reconstituted thyme infusion occurs very quickly. After 90 sec infusion, optical density of original material is 2.3 whereas liquor from reconstituted thyme optical density is 5.3 which is 130% higher.

Example 14

Reconstitution of Thyme and Black Tea Leaves

A reconstituted product was made according to the following method: Thyme (*Thymus vulgaris*) and black tea (*Camelia sinensis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a blend/water ratio of 1 to 5 by weight. After an additional extraction (by pressing), the fibrous portion was then refined in a Valley beater at 1.4% consistency for 10 minutes, After refining, cellulosic fibers (a blend of abaca, hardwood and softwood pulps, with the respective ratios: 60/10/30) were added to the blend fibrous residue with a blend fiber/wood pulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 25% extract content, which is the balanced soluble content of the materials of the experiment. The coated hand sheets were dried on a plate dryer.

Figure 15:
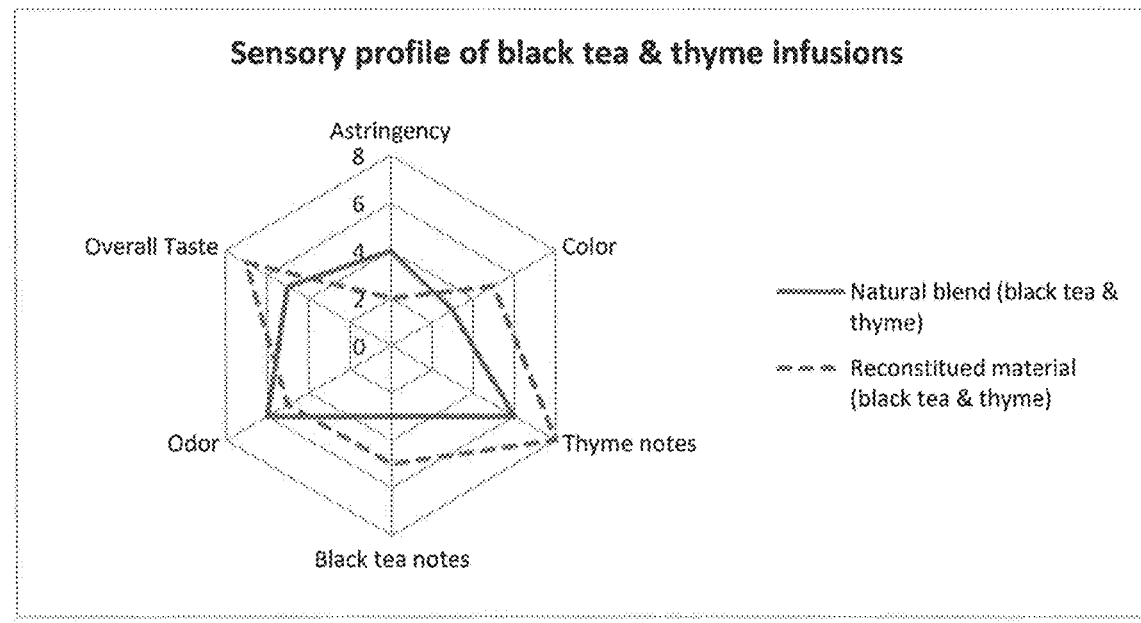
FIG. 15 shows the sensory analysis of reconstituted thyme & black tea as compared to the natural blend.

The product obtained in this example was tested for its sensory properties and compared to natural blend material used for the experiment as described above. Both products were used to make the infusion. For all samples, the total infusion time in hot water (90° C.) was 5 minutes. Same weights of material (2 grs) and identical experimental conditions were used: a beaker containing 200 ml water was heated at 90° C. and blend was immersed into water. Then, after 5 minutes, sensory profile of both products was performed. The result is graphically shown in FIG. 15.

The experiment shows that color and overall taste are higher in the reconstituted leaves. Also, thyme and black tea notes are higher. But the astringency of the product is lower in the reconstituted material.

Example 15

Reconstitution of Thyme and Laurel Leaves ("Bouquet Garni")

A reconstituted product was made according to the following method: Thyme (*Thymus vulgaris*) and Laurel (*Laurus nobilis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the blend fibrous residue with a blend fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 34% extract content which is the balanced soluble content of the materials of the experiment. The coated hand sheets were dried on a plate dryer.

Figure 16:
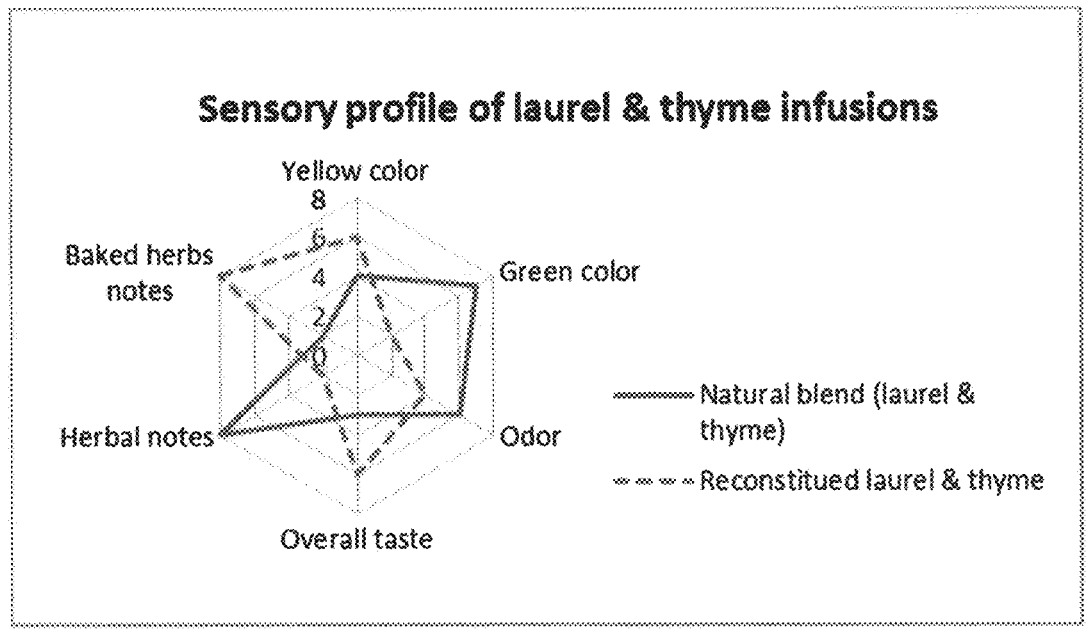
FIG. 16 shows the sensory analysis of reconstituted laurel & thyme vs natural blend (laurel & thyme leaves).

The product obtained in this example was tested for its sensory properties and compared to natural tea material used for the experiment as described above. Both products were used to make tea. For all samples, the total infusion time in hot water (90° C.) was 5 minutes. Same weights of tea material (2 grs) and identical experimental conditions were used: a beaker containing 200 ml water was heated at 90° C. and tea materials were immersed into water. Then, after 5 minutes, sensory profile of both products was performed. The result is graphically shown in FIG. 16.

The experiment shows that the two products are very different. The color is rather yellow for reconstituted product and green for the original blend. The taste is on the herbal side for the original blend and more on the baked side for the reconstituted material. Globally, taste and odor are higher for the original blend. Taste and odor can, however be adjusted and increased for the reconstituted material by increasing soluble content of reconstituted material or by adding ingredients such as food flavors, food dyes or other plant extracts having color and aroma properties.

Example 16

Reconstitution of Mint Leaves

A reconstituted product was made according to the following method: Mint (*Mentha×piperita*) was initially heated at 85° C. for 20 minutes with a mint/water ratio of 1 to 5 by weight. This was followed by an extraction step in a hydraulic press to separate the aqueous portion from the rooibos fiber portion. The recovered mint fiber portion was again heated at 85° C. for 10 minutes with a mint water ratio of 1 to 5 by weight. After an additional extraction (by pressing), the fibrous portion was then refined in a Valley beater at 1.4% consistency for 10 minutes. After refining, cellulosic fibers (a blend of ahaca, hardwood and softwood pulps, with the respective ratios: 60/10/30) were added to the mint fibrous residue with a mint fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 50% extract content, which is the soluble content of the starting material of the experiment. The coated hand sheets were dried on a plate dryer.

Figure 17:
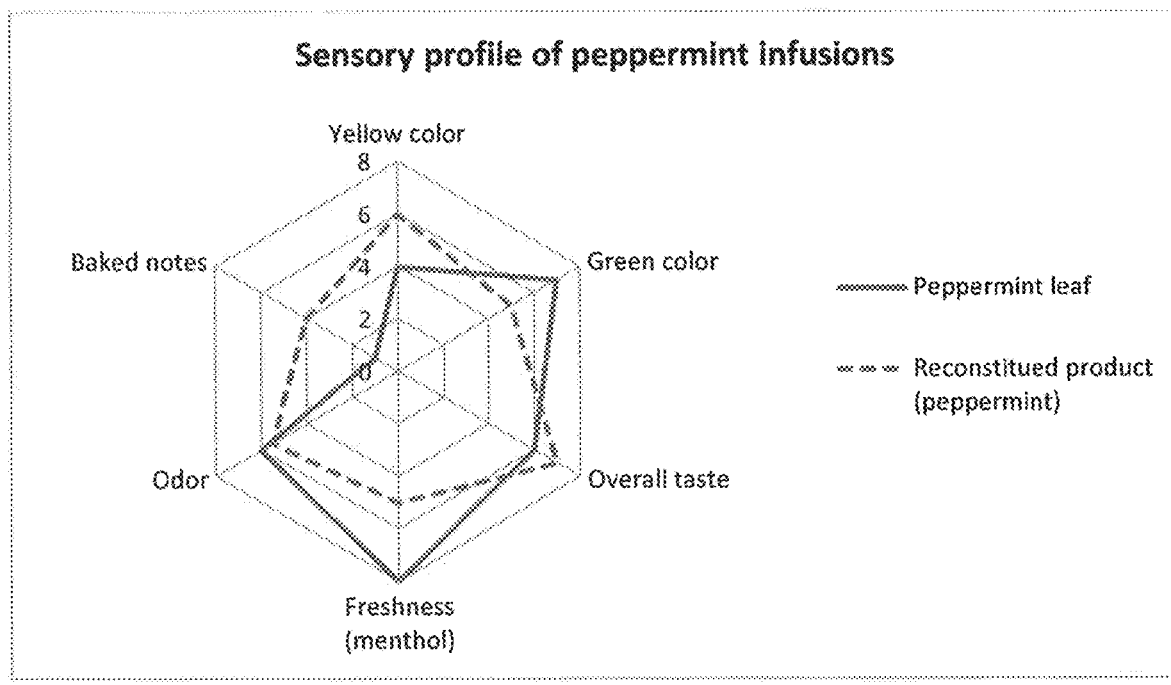
FIG. 17 shows the sensory analysis of reconstituted mint vs original mint material (*Mentha×piperita*).

The product obtained in this example was tested for its sensory properties and compared to natural mint material used for the experiment as described above. Both products were used to make a mint beverage. For all samples, the total infusion time in hot water (90° C.) was 5 minutes. Same weights of mint material (2 grs) and identical experimental conditions were used: a beaker containing 200 ml water was heated at 90° C. and mint material was immersed into water. Then, after 5 minutes, sensory profile of both products was performed. The result is graphically shown in FIG. 17.

The experiment shows that in the reconstituted product, freshness/menthol notes have been reduced vs original mint material; however, overall taste is stronger.

Example 17

Reconstitution of Mint (*Mentha×piperita*) and Green Tea Leaves (*Camellia sinensis*)

A reconstituted product was made according to the following method: Mint (*Mentha×piperita*) and Green Tea leaves (*Camellia sinensis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a blend/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the blend fibrous residue with a blend fiber/wood pulp ratio of 5 to 1 in weight in order to make hand sheets. The aqueous portion was concentrated in an evaporator to a solid concentration of 50% and L-menthol was added to the solution at 6% and then coated on a hand sheet on a manual size-press. In this example, the product was produced at 35% extract content, which is the balanced soluble content of the materials of the experiment. The coated hand sheets were dried on a plate dryer.

Figure 18:
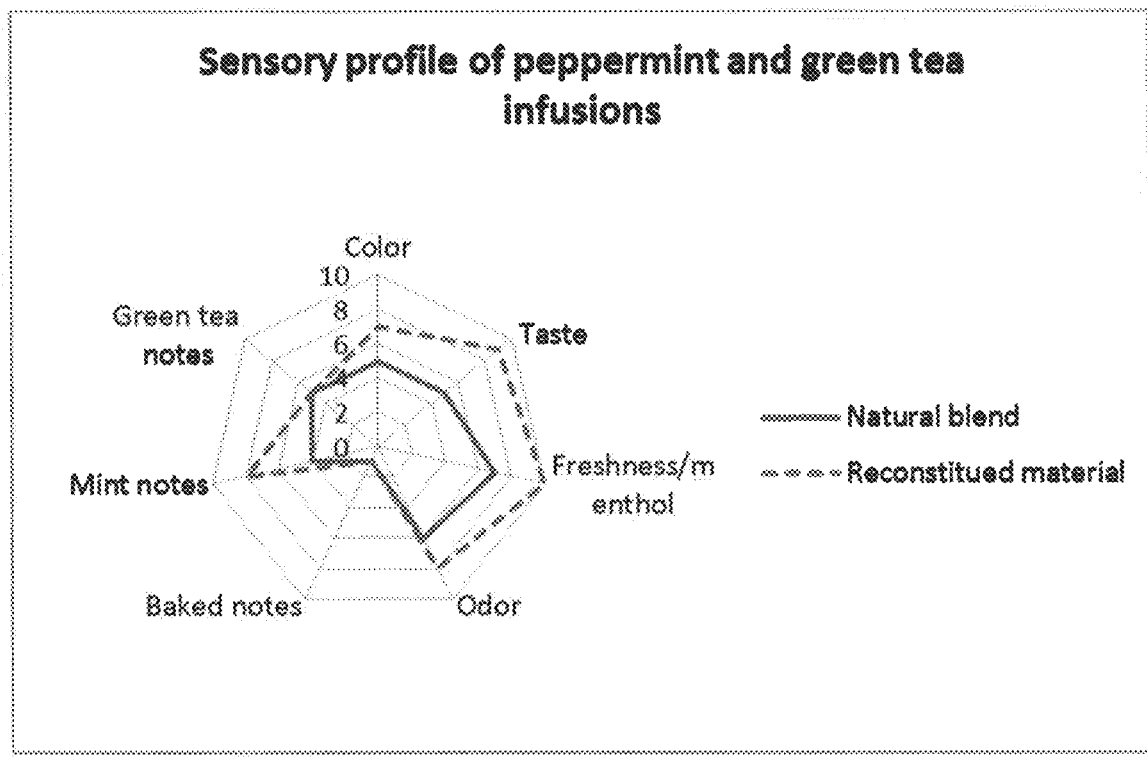
FIG. 18 shows the sensory analysis of reconstituted mint and green tea vs original blend.

The product obtained in this example was tested for its sensory properties and compared to natural blend material used for the experiment as described above. Both products were used to make the infusion. For all samples, the total infusion time in hot water (90° C.) was 5 minutes. Same weights of material (2 grs) and identical experimental conditions were used: a beaker containing 200 ml water was heated at 90° C. and blend was immersed into water. Then, after 5 minutes, sensory profile of both products was performed. The result is graphically shown in FIG. 18.

Example 18

Removal of Caffeine from Tea Leaves Thanks to the Reconstitution Process

In order to illustrate the potential of the invention to reduce the amount of specific components from tea, a treatment to decrease caffeine content from tea was developed and tested at the lab scale.

Literature shows that alkaloids compounds such as caffeine are extracted in the soluble portion. Therefore, experiment has been run on the liquor part of tea, after separation step.

A black tea was initially heated at 85° C. for 20 minutes with a tea water ratio of 1 to 5 by weight. This was followed by an extraction step in a hydraulic press to separate the aqueous portion from the tea fiber portion. The aqueous portion of tea was then mixed with activated charcoal in powder form. Approx. 23 g of activated charcoal was added to 500 ml of tea liquor and mixed at 60° C., stirred at 350 rpm for 1 hour. After filtration, caffeine levels in liquors were measured then through LC-MS method.

The following samples were produced:
Control: standard tea liquor without activated charcoal treatment
A: Tea liquor treated with activated charcoal Acticarbone P13 from CECA
B: Tea liquor treated with activated charcoal Acticarbone 2SW from CECA
C: Tea liquor treated with activated charcoal Acticarbone 3SA from CECA
D: Tea liquor treated with activated charcoal Acticarbone CPL from CECA
Caffeine contents in tea liquors are as follows:
Control: 22700 mg/Kg
A: <10 mg/Kg
B: <10 mg/Kg
C: <10 mg/Kg
D: <14 mg/Kg It can be seen that caffeine levels are strongly reduced by using activated charcoal on tea liquor.

Example 19

Reduction of Microbiological Load of Tea through the Reconstituted Process

Reconstituted tea material produced during experiment 7 was analyzed vs original tea material. Bacteria counts were run (Aerobic Plate Count after 48 hrs at 30° C.). Results are shown in the following table:

|  | Total Aerobic bacteria count (units/grs) |
| --- | --- |
| Original tea material | $8.3 \cdot 10^4$ |
| Reconstituted teas | $1.4 \cdot 10^3$ |

Results show that reconstitution process does reduce the microbiological load. Temperatures applied all along the process have a lethal effect of microorganisms.

Example 20

Reconstituted material was produced in different physical shapes that provide for different kinds of applications. Specifically, the products shown in FIG. 19 are examples that allow for convenient preparation of tea infusions.

Example 21

A reconstituted product was made according to the following method: coffee (*Coffea* spp) was initially heated at 60° C. for 20 minutes with a coffee/water ratio of 1 to 5 by weight. This was followed by an extraction step in a hydraulic press to separate the aqueous portion from the coffee fiber portion. The recovered coffee fiber portion was again heated at 60° C. for 10 minutes with a coffee/water ratio of 1 to 5 by weight. After an additional extraction (by pressing), the fibrous portion was then refined in a Valley beater at 1.4% consistency for 10 minutes. After refining, cellulosic fibers (a blend of abaci, hardwood and softwood pulps, with the respective ratios: 60/10/30) were added to the coffee fibrous residue with a coffee fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 30% extract content, which is the soluble content of the starting material of the experiment. The coated hand sheets were dried on a plate dryer.

The product obtained in this example was tested for its properties in preparing coffee and compared to original material. Both products were used to make coffee, and the optical density of the solution (coffee) was measured at 274 nm. For all samples, the total infusion time in hot water (90° C.) was 5 minutes. Same weights of coffee material (2.5 grs) and identical experimental conditions were used: a beaker containing 500 ml water was heated at 90° C. At T=0, ie. upon start of the experiment, heating was stopped and a coffee strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 274 nm (maximum absorption of caffeine). The reference/blank test was run with a sample of clear water heated at 90° C.

Figure 20:
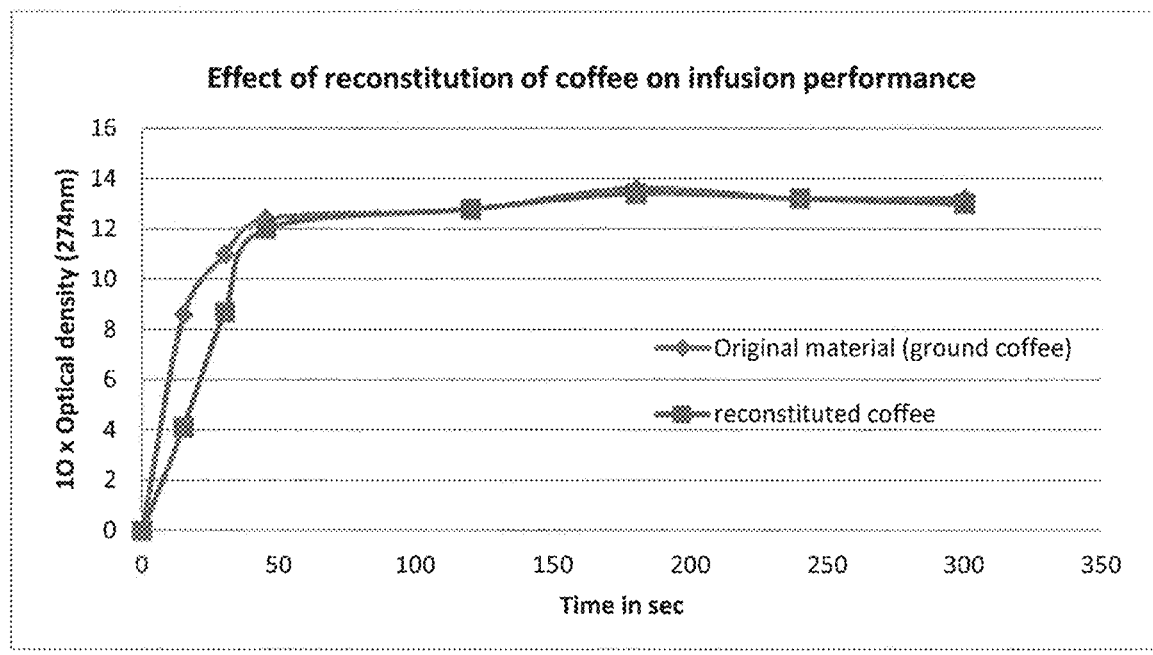
FIG. 20 shows the infusion performance of a reconstituted coffee material.

The result is graphically shown in FIG. 20 below.

While infusion prepared with original coffee material is faster during the first 50 seconds, after 1 minute, infusion profiles of both samples are similar.

The invention claimed is:

1. A product for producing a beverage or broth comprising:
a dispenser defining an opening; and
an infusion product comprising a strip made from a layer comprising an insoluble fibrous plant material and a plant extract that is dispensed through the opening defined by the dispenser,
wherein at least a portion of the plant extract and at least a portion of the insoluble fibrous plant material are from the same plant, wherein the insoluble fibrous plant material is impregnated with the plant extract, and wherein the product has an optical density at 274 nm of greater than about 0.4 after 2.5 grams of the product are immersed in 500 mL of water at a temperature of 90° C. for 20 seconds.

2. A product as defined in claim 1, wherein the strip comprises a single continuous strip contained within the dispenser.

3. A product as defined in claim 2, wherein the single continuous strip includes periodic perforation lines that extend across a width of the strip.

4. A product as defined in claim 1, wherein the strip comprises a plurality of individual strips contained within the dispenser.

5. A product as defined in claim 4, wherein each individual strip includes a tab portion.

6. A product as defined in claim 5, wherein the tab portion comprises a separate piece of material connected to the layer of insoluble fibrous plant material or comprises a coating applied to the layer of insoluble fibrous plant material.

7. A product as defined in claim 4, wherein each individual strip includes an adhesive portion, the adhesive portion comprising an adhesive material.

8. A product as defined in claim 7, wherein the adhesive portion includes a release liner that covers the adhesive material.

9. A product as defined in claim 4, wherein the individual strips are connected together.

10. A product as defined in claim 4, wherein the individual strips are separate and discrete within the dispenser.

11. A product as defined in claim 1, wherein the dispenser further includes a cutting device positioned adjacent the opening for cutting the infusion product as the infusion product is dispensed from the dispenser.

12. A product as defined in claim 1, wherein the infusion product is spirally wound within the dispenser.

13. A product as defined in claim 1, wherein the insoluble fibrous plant material comprises a tea.

14. A product as defined in claim 13, wherein the layer of insoluble fibrous plant material comprises at least 70% by weight of the tea.

* * * * *